US008968719B2

(12) United States Patent
Kopecko et al.

(10) Patent No.: US 8,968,719 B2

(45) **Date of Patent: *Mar. 3, 2015**

(54) **LIVE, ORAL VACCINE FOR PROTECTION AGAINST *SHIGELLA DYSENTERIAE* SEROTYPE 1**

(71) Applicant: The United States of America, as represented by the Secretary, Department of Health and Human Services, Rockville, MD (US)

(72) Inventors: Dennis J. Kopecko, Silver Spring, MD (US); De-Qi Xu, Columbia, MD (US)

(73) Assignee: The United States of America, as represented by the Secretary, Department of Health and Human Sevices, Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/145,104

(22) Filed: Dec. 31, 2013

(65) Prior Publication Data

US 2014/0120134 A1 May 1, 2014

Related U.S. Application Data

(63) Continuation of application No. 13/687,797, filed on Nov. 28, 2012, now Pat. No. 8,790,635, which is a continuation of application No. 13/285,614, filed on Oct. 31, 2011, now Pat. No. 8,337,831, which is a continuation of application No. 11/597,301, filed as application No. PCT/US2005/018198 on May 24, 2005, now Pat. No. 8,071,113.

(60) Provisional application No. 60/609,494, filed on Sep. 13, 2004, provisional application No. 60/574,279, filed on May 24, 2004.

(51) Int. Cl.

| | |
|---|---|
| ***A61K 48/00*** | (2006.01) |
| ***A61K 39/02*** | (2006.01) |
| ***A61K 39/116*** | (2006.01) |
| ***A61K 39/112*** | (2006.01) |
| ***C07K 14/25*** | (2006.01) |
| ***C12N 15/52*** | (2006.01) |
| *A61K 39/00* | (2006.01) |

(52) U.S. Cl.

CPC ............. *A61K 39/0283* (2013.01); *A61K 48/00* (2013.01); *A61K 2039/522* (2013.01); *A61K 2039/523* (2013.01); *C07K 14/25* (2013.01); *C12N 15/52* (2013.01)

USPC ... 424/93.2; 424/93.1; 424/184.1; 424/200.1; 424/203.1; 424/234.1; 536/23.1; 536/23.7

(58) Field of Classification Search

CPC ............. C07H 21/04; A61K 2039/522; A61K 2039/523; A61K 39/0275; A61K 39/0283; C07K 14/25; C12N 15/00; C12N 15/63

USPC ........... 536/23.1, 23.7; 424/93.1, 93.2, 184.1, 424/200.1, 203.1, 234.1

See application file for complete search history.

(56) References Cited

U.S. PATENT DOCUMENTS 8,071,113 B2 * 12/2011 Kopecko et al. ........... 424/258.1
8,337,831 B2 * 12/2012 Kopecko et al. ............ 424/93.2

OTHER PUBLICATIONS

Baron (1987) Infect Immun; 55:2797-2801.
Black (1987) J Infect Dis; 155:1260-1265.
Churchward (1984) Gene; 31:165-171.
Datsenko (2000) Proc Natl Acad Sci USA; 97:6640-6645.
Dmitriev (1976) Eur J Biochem; 66:559-566.
Dupont (1989) J Infect Dis; 159:1126-1128.
Dworkin (2001) Clin Infect Dis; 33:1010-1014.
EMBL Database (1992) Accession No. L07293.
EMBL Database (1992) Accession No. M96064.
EMBL Database (1995) Accession No. S73325.
EMBL Database (2001) Accession No. AF402313.
EMBL Databae (2002) Accession No. AF529080.
Engels (1998) BMJ; 316:110-116.
European Search Report Issued Dec. 13, 2012 in EP 12186545.5.
Extended European Search Report Issued Oct. 2, 2013 in EP 13176694.1.
Falt (1995) J Bacteriol; 177:5310-5315.
Falt (1996) Microb Pathog; 20:11-30.
Favre (1996) Infect Immun; 64:576-584.
Feng (2004) Microb Pathog; 36:109-115.
Feng (2007) Microbiology; 153:139-147.
Fernandez (2003) Cell Microbiol; 5:481-491.
Formal (1981) Infect Immun; 34:746-750.
Franco (1996) J Bacteriol; 178:1903-1907.
Gentry (1980) J Clin Microbiol; 12:361-366.
Gentschev (2007) Chemitherapy; 53:177-180.
Germanier (1971) Infect Immun; 4:663-673.
Germanier (1975) J Infect Dis; 131 :553-558.

(Continued)

*Primary Examiner* — Rodney P Swartz

(74) *Attorney, Agent, or Firm* — Swanson & Bratschun, L.L.C.

(57) ABSTRACT

The invention relates to *Salmonella typhi* Ty21a comprising core-linked *Shigella dysenteriae* serotype 1 O-specific polysaccharide (O-Ps) and DNA encoding O antigen biosynthesis, said DNA selected from the group consisting of: a) the DNA sequence set out in any one of SEQ ID NOs: 1 and 2 and species homologs thereof; b) DNA encoding *Shigella dysenteriae* serotype 1 polypeptides encoded by any one of SEQ ID NOs: 1 and 2, and species homologs thereof; and c) DNA encoding a O antigen biosynthesis gene product that hybridizes under moderately stringent conditions to the DNA of (a) or (b); and related sequences, compositions of matter, vaccines, methods of using, and methods of making.

2 Claims, 5 Drawing Sheets

(56) References Cited

OTHER PUBLICATIONS

Hale (1984) Infect Immun: 46:470-475.
Hartman (1991) J Clin Microbiol; 29:27-32.
Herrington (1990) Vaccine; 8:353-357.
Hoare (2006) Infect Immun; 74:1555-1564.
IPRP for PCT/US2005/018198; Nov. 29, 2006.
ISR for PCT/US2005/018198; Oct. 10, 2005.
Ivanoff (1994) Bull Who; 72:957-971.
Johnson (1994) Infect Immun; 62:2108-2110.
Klee (1997) Infect Immun; 65:2112-2118.
Klee (1997) J Bacteriol; 179:2421-2425.
Klena (1992) J Bacteriol; 174:7297-7307.
Klena (1993) Mol Microbiol; 9:393-402.
Kotloff (1999) Bull Who; 77:651-666.
Levine (1982) Med Clin North Am; 66:623-639.
Levine (1999) Vaccine; 17:S22-S27.
Maurelli (1998) Microb Pathog; 25:189-196.
Mendizabal-Morris (1971) Am J Trop Med Hyg; 20:927-933.
Mills (1988) Vaccine; 6:116-122.
Nandy (1999) Vaccine; 17:2844-2852.
Neill (1988) J Infect Dis; 158:737-741.
Noriega (1999) Infect Immun; 67:782-788.
Office Action for EP 05754091; Aug. 24, 2007.
Office Action for EP 05754091; May 13, 2009.
Office Action for EP 05754091; Sep. 22, 2010.
Oberhelman (1991) Bull Who; 69:667-676.
Oberhelman (1991) Infect Immun; 59:2341-2350.
Peleg (2005) J Bacteriol; 187:5259-5266.
Pupo (1997) Infect Immun; 65:2685-2692.
Raqib (2000) Infect Immun; 68:3620-3629.
Sansonetti (2006) Ann NY Acad Sci; 1072:307-312.
Schnaitman (1993) Microbiol Rev; 57:655-682.
Seid (1984) J Biol Chem; 259:9028-9034.
Simmons (1969) Eur J Bioch Em; 11 :554-575.
STurm (1986) Microb Pathog; 1:289-297.
Sturm (1986) Microb Pathog; 1:307-324.
UniProt Database (1995) Accession No. Q03583.
UniProt Database (1995) Accession No. Q03584.
UniProt Database (1996) Accession No. Q03581.
UniProt Database (1996) Accession No. Q03582.
UniProt Database (1996) Accession No. Q53982.
Un I Prot Database (2001) Accession No. Q93CU2.
Un I Prot Database (2001) Accession No. Q93CV2.
Un I Prot Database (2001) Accession No. Q93CV3.
UniProt Database (2002) Accession No. AAU09677.
UniProt Database (2005) Accession No. Q51ZD4.
UniProt Database (2005) Accession No. Q51ZD5.
UniProt Database (2005) Accession No. Q51ZD6.
UniProt Database (2005) Accession No. Q51ZD7.
Vi Rei (1994) Biologicals; 22:361-372.
Wang (2001) Infect Immun; 69:6923-6930.
Watanabe (1984) Infect Immun; 43:391-396.
World Health Organization (1997) Weekly Epidemiological Report; 72:73-80.
Winsor (1988) J Infect Dis; 158:1108-1112.
Xu (2002) Infect Immun: 70:4414-4423.
Xu (2007) Vaccine; 25:6167-6175.

* cited by examiner

Fig. 1 The genes necessary for biosynthesis of the *S. dysenteriae* 1 O-antigen
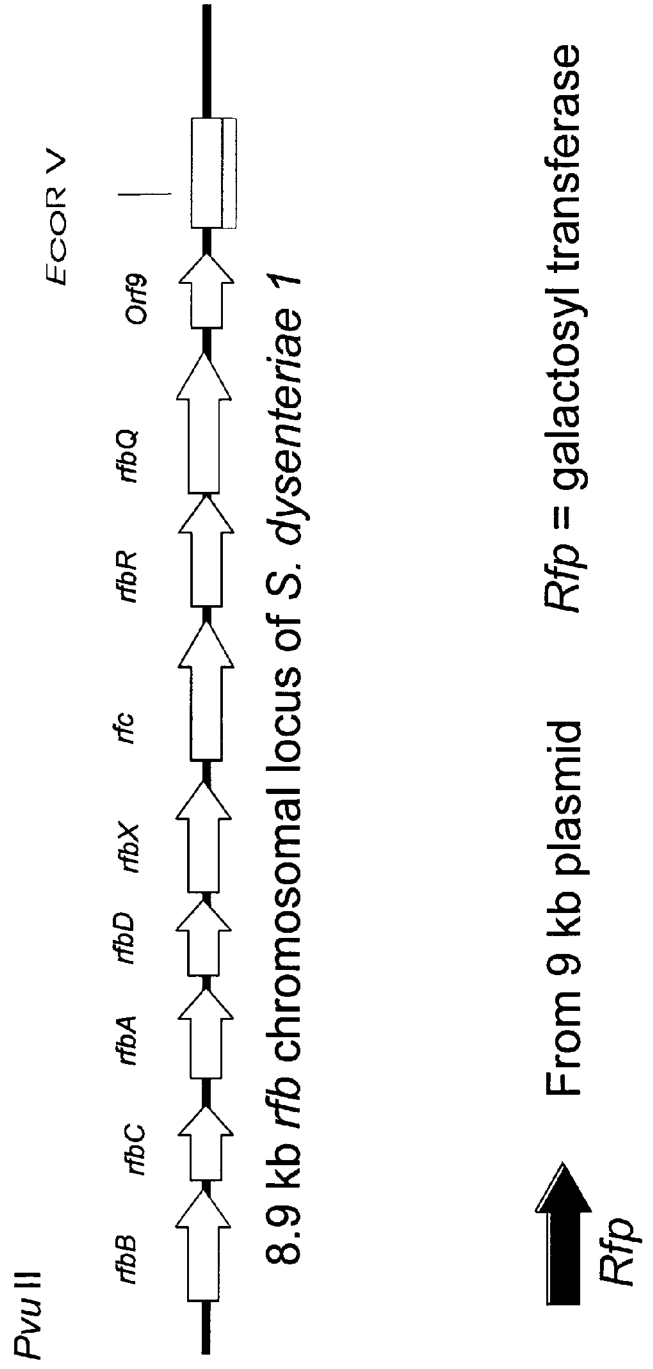

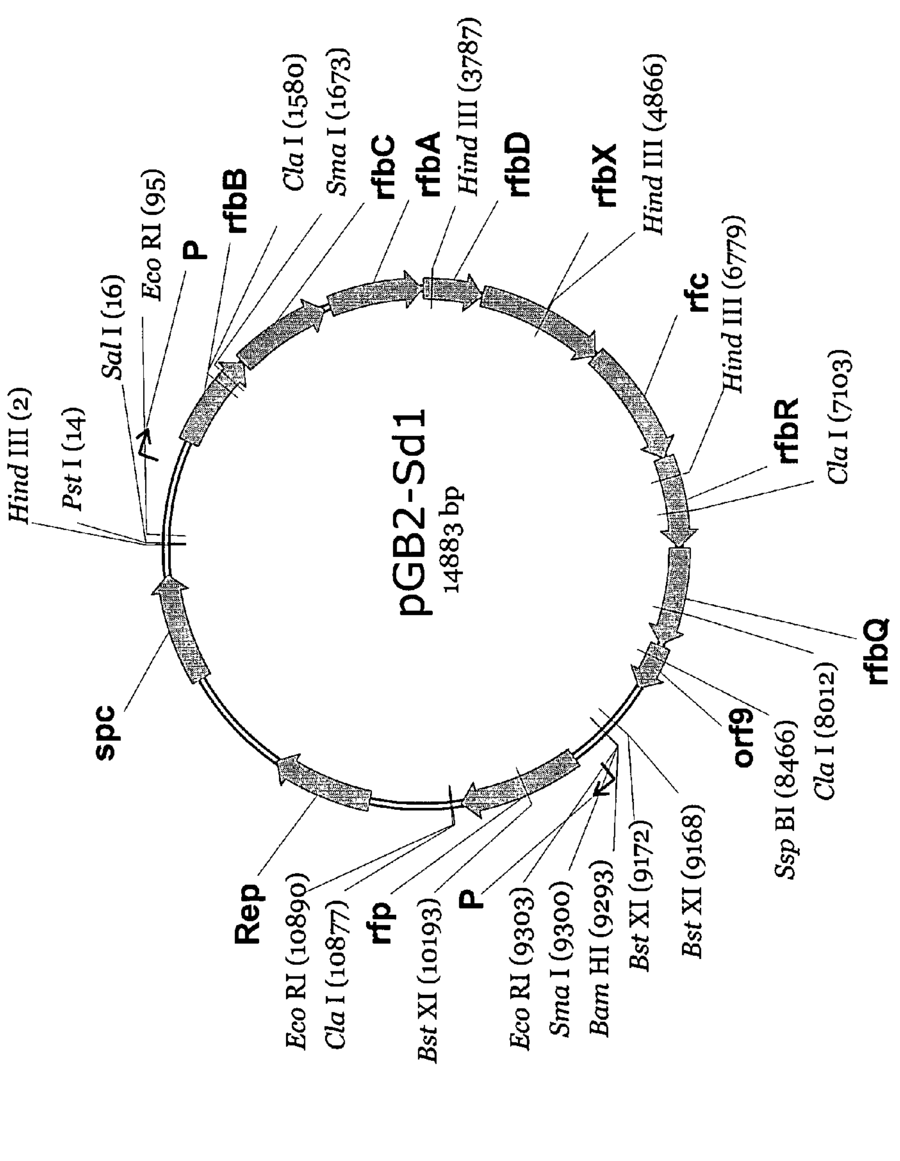
Fig 2. *E. coli* (pGB2-Sd1) was found to express *S. dysenteriae* 1 O-antigen by both slide agglutination and immunoblot assays using *S. dysenteriae* 1-specific antisera.

**Fig. 3 Proposed sugar transferase requirements for synthesis of the *Shigella dysenteriae* type 1 O-polysaccharide repeat unit.**

RfbR RfbQ Rfp Rfe

→2)α-Rha III-(1→3)-α-L-Rha I-(1-2)-α-D-Gal I-(1 →3) - α - D-GlcNAc-(1→ ACL

*Rfe* is a GlcNac transferase which adds GlcNAc to ACL (antigen carrier lipid/ acyl lipid carrier/undecaprenol phosphate); *RfbR* and *RfbQ* are Rha transferases; *Rfp* is a galactosyl transferase. (Mol. Microbiol. 1995, 18:209)

LIVE, ORAL VACCINE FOR PROTECTION AGAINST *SHIGELLA DYSENTERIAE* SEROTYPE 1

CROSS-REFERENCE TO RELATED APPLICATIONS

This application is a continuation of U.S. patent application Ser. No. 13/687,797, filed Nov. 28, 2012, which was allowed on Nov. 18, 2013, and which is a continuation of U.S. patent application Ser. No. 13/285,614, filed Oct. 31, 2011, now U.S. Pat. No. 8,337,831, issued Dec. 25, 2012; which is a continuation of U.S. patent application Ser. No. 11/597,301, filed Sep. 21, 2007, now U.S. Pat. No. 8,071,113, issued Dec. 6, 2011; which is a national phase entry pursuant to 35 U.S.C. §371 of International Patent Application No. PCT/US2005/018198, filed May 24, 2005; which application claims the benefit of U.S. Provisional Patent Application No. 60/609,494, filed Sep. 13, 2004, and U.S. Provisional Patent Application No. 60/574,279, filed May 24, 2004; the disclosures of all of the foregoing applications are incorporated herein by reference in their entireties.

STATEMENT REGARDING FEDERALLY SPONSORED RESEARCH OR DEVELOPMENT

The instant application was made with government support; the government has certain rights in this invention.

SEQUENCE LISTING

The Sequence Listing text file attached hereto, created Nov. 28, 2012, size 42 kilobytes, and filed herewith as file name "6137FDA3PUS11_SEQ_20121128_ST25.txt" is incorporated herein by reference in its entirety.

BACKGROUND OF THE INVENTION

*Shigella* cause millions of cases of dysentery (i.e., severe bloody diarrhea) every year, which result in 660,000 deaths worldwide. *Shigella dysenteriae* serotype 1, one of about 40 serotypes of *Shigella*, causes a more severe disease with a much higher mortality rate than other serotypes. There are no FDA-licensed vaccines available for protection against *Shigella*, although a number of institutions are trying various vaccine approaches. The fact that many isolates exhibit multiple antibiotic resistance complicates the management of dysentery infections. The development of an immunogenic composition against *Shigella dysenteriae* serotype 1 therefore represents a particularly urgent objective.

SUMMARY OF THE INVENTION

The invention relates to *Salmonella typhi* Ty21a comprising core-linked *Shigella dysenteriae* serotype 1 O-specific polysaccharide (O-Ps) and DNA encoding O antigen biosynthesis, said DNA selected from the group consisting of:

(a) the DNA sequence set out in any one of SEQ ID NOs: 1 and 2 and species homologs thereof;

(b) DNA encoding *Shigella dysenteriae* serotype 1 polypeptides encoded by any one of SEQ ID NOs: 1 and 2, and species homologs thereof; and (c) DNA encoding a O antigen biosynthesis gene product that hybridizes under moderately stringent conditions to the DNA of (a) or (b);

and related sequences, compositions of matter, vaccines, methods of using, and methods of making.

BRIEF DESCRIPTION OF THE DRAWINGS

FIG. 1. The genes necessary for biosynthesis of the *Shigella dysenteriae* serotype 1O-antigen.

FIG. 2. *E. coli* (pGB2-Sd1) was found to express *Shigella dysenteriae* serotype 1 O-antigen by both slide agglutination and immunoblot assays using *Shigella dysenteriae* serotype 1-specific antisera.

FIG. 3. Proposed sugar transferase requirements for synthesis of the *Shigella dysenteriae* serotype 1 O-polysaccharide repeat unit. Rfe is a GlcNac transferase which adds GlcNAc to ACL (antigen carrier lipid/acyl lipid carrier/undecaprenol phosphate); RfbR and RfbQ are Rha transferases; Rfp is a galactosyl transferase (*Mol. Microbial.* 1995, 18:209)

SEQUENCE SUMMARY

Figure 4A:
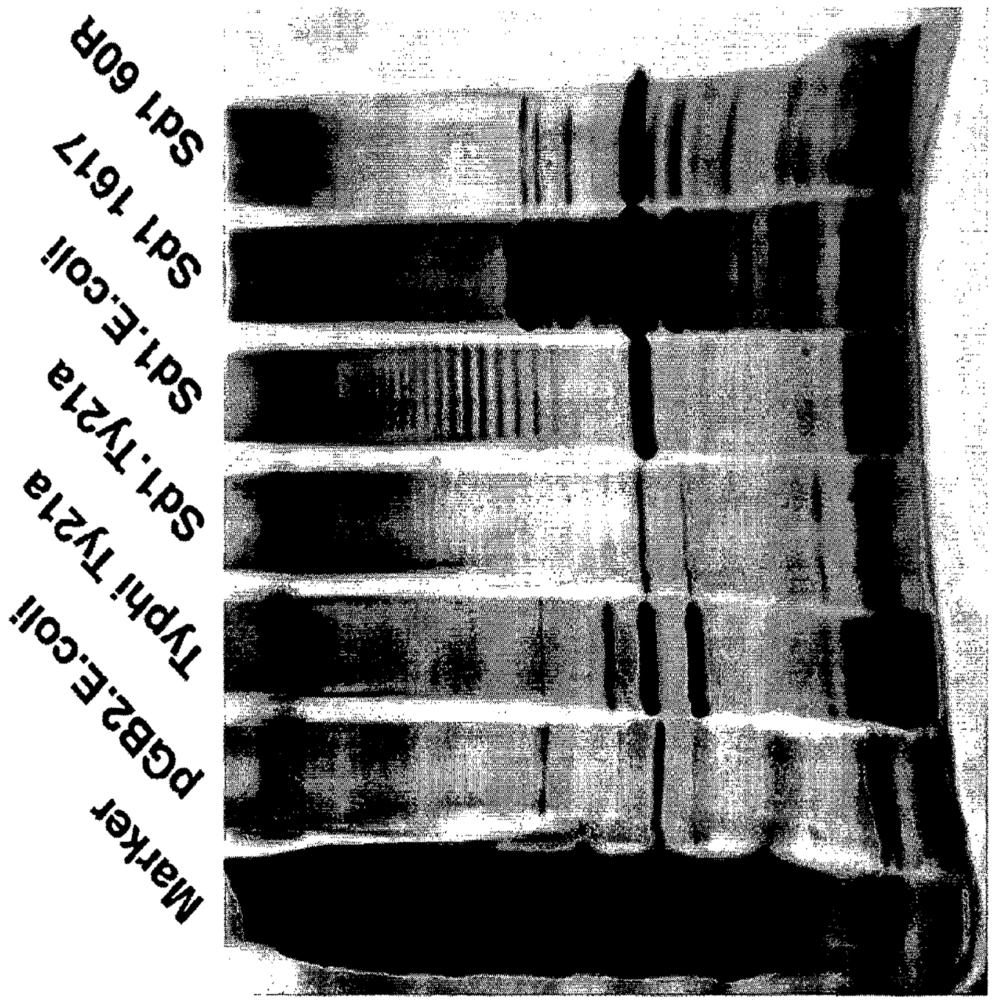
FIGS. 4A-4B. Expression analyses of LPS from various parental and plasmid-carrying strains. LPS was extracted from various strains as described below and separated on SDS-PAGE gels by electrophoresis. Resulting silver-stained material (A) and a Western immunoblot (B) reacted with anti-*Shigella dysenteriae* serotype 1 antisera are shown. In both parts (A) and (B), molecular weight markers are shown in the left-hand lane followed by extracted polysaccharide from *E. coli* carrying pGB2 (lane pGB2.*E. coli*), parent *S. typhi* Ty21a (lane *Typhi* Ty21a), Ty21a carrying pGB2-Sd1 (lane Sd1.Ty21a), *E. coli* carrying pGB2-Sd1 (lane Sd1.*E. coli*), the parent *Shigella dysenteriae* serotype 1 strain 1617 (lane Sd1 1617), or the rough *Shigella dysenteriae* serotype 1 strain 60R (lane Sd1 60R).

| SEQ ID NO. | Description |
|---|---|
| 1 | 9297 bp. Sequence of rfb locus of *Shigella dysenteriae* serotype 1 strain 1617 |
| 2 | 1507 bp. rfp Sequence from *Shigella dysenteriae* serotype 1 strain 1617. |
| 3 | rfbB |
| 4 | rfbC |
| 5 | rfbA |
| 6 | rfbD |
| 7 | rfbX |
| 8 | rfc |
| 9 | rfbR |
| 10 | rfbQ |
| 11 | orf9 |
| 12 | rfp |

DETAILED DESCRIPTION OF THE PREFERRED EMBODIMENT

*Shigella dysenteriae* serotype 1 causes the most severe form of shigellosis, often associated with hemolytic uremic syndrome in children, especially in developing countries. Due to the high level of Shiga toxin production and associated high morbidity/mortality, this organism is classified as a Category B bioterrorist threat agent. The lipopolysaccharide of *Shigella dysenteriae* serotype 1 is essential for virulence, and there is indirect evidence that antibodies against this O-specific polysaccharide (O-Ps) are protective to the host. Thus, there is considerable interest in the development of an O-Ps-based vaccine to protect against *Shigella dysenteriae* serotype 1. Previous studies showed that the determinants for the production of 0 antigen lipopolysaccharide in *Shigella dysente-*

*riae* serotype 1 are distributed on the chromosome (i.e., rfb/rfc genes) and on a small 9-kb plasmid (i.e., rfp gene). The current studies were aimed at cloning the Rfb/Rfc region from strain 1617 to define all essential genes and develop a biosynthetic pathway for O-Ps biosynthesis. The plasmid-carried gene (i.e., the rfp-encoded galactosyl transferase) was also cloned from strain 1617; its 1.6 kb sequence was found to be >99% homologous to rfp previously analyzed from a different *Shigella dysenteriae* serotype 1 strain. Additionally, the chromosomal Rfb/Rfc region of 9 kb was cloned and sequenced, and found to contain 9 ORFs. Preliminary analysis suggests that all 9 ORFs plus rfp are necessary for serotype 1 LPS biosynthesis. We anticipate that the use of these characterized O-Ps genes in a live, attenuated *Salmonella* delivery system will lead to a safe, oral vaccine for protection against this severe form of shigellosis.

Introduction

*Shigella* spp. are the predominant cause of acute bloody diarrhea (dysentery) worldwide, and cause 660,000 deaths globally each year due to shigellosis. Infection with *Shigella dysenteriae* serotype 1 strains causes a more severe illness with higher mortality than with other *Shigellae*, particularly in young children and the elderly.

Protective immunity against shigellosis appears to be serotype-specific and protection correlates with the stimulation of immunity against the O-specific surface lipopolysaccharide.

The genes necessary for O-Ps synthesis in *Shigella dysenteriae* serotype 1 lie on a 9-kb small plasmid (i.e., the rfp gene) and on the chromosome (i.e., rfb cluster). A recombinant plasmid containing the essential *Shigella dysenteriae* serotype 1 O-antigen biosynthetic genes was previously constructed and introduced into *E. coli* or attenuated *Salmonella* spp. This plasmid construct was reported to be unstable when the strains were cultivated without selective pressure, and animal immunization resulted in less than 50% protection (Klee, S. R. et al. 1997 *J Bacteriol* 179:2421-2425).

The current studies were aimed at cloning the essential O-Ps biosynthetic machinery of *Shigella dysenteriae* serotype 1, deleting unnecessary adjacent sequences, and completing the DNA sequence analysis of the entire biosynthetic region to define a minimal essential set of genes.

Materials and Methods

1. *Shigella dysenteriae* serotype 1 strain 1617 was obtained from the culture collection of S. B. Formal, Walter Reed Army Institute of Research (WRAIR). The strain was originally isolated from an outbreak of epidemic Shiga *bacillus* dysentery in Guatemala, Central America, in 1968 (Mendizabal-Morris, C A. et al. 1971 *J Trop Med Hyg* 20:927-933). Plasmid and chromosomal DNA used in this study was prepared from this strain.

2. The plasmid rfp region and its cognate promoter and a ~9.5 kb rfb locus were first cloned into the pCR 2.1-TOPO vector separately. The insert DNA was confirmed by DNA sequence analysis, and then transferred into the low copy plasmid pGB2 for genetic stabilization.

3. DNA sequence analysis and BLAST homology searches were employed to characterize the essential biosynthetic gene region.

4. The parent *Shigella dysenteriae* serotype 1 strain 1617 and recombinant *E. coli* strains expressing the *Shigella dysenteriae* serotype 1 O-Ps were analyzed for expression by agglutination and immunoblot assays with specific anti-*Shigella dysenteriae* serotype 1 LPS antisera (Difco, Detroit).

TABLE 1

Summary of *Shigella dysenteriae* serotype 1 O-Ps ORFs

| ORF | Gene name | Location | Proposed function |
|---|---|---|---|
| 1 | rfbB | 756-1841 | dTDP-D-glucose 4,6 dehydratase |
| 2 | rfbC | 1841-2740 | dTDP-4-dehydrorhamnose reductase |
| 3 | rfbA | 2798-3676 | Glucose-I-phosphate thymilytransferase |
| 4 | rfbD | 3679-4236 | dTDP-4-dehydrorhamnose 3,5-epimerase |
| 5 | rfbX | 4233-5423 | O-Ag transporter |
| 6 | rfc | 5420-6562 | O-Ag polymerase |
| 7 | rfbR | 6555-7403 | dDTP-rhamnosyl transferase |
| 8 | rfbQ | 7428-8339 | Rhamnosyltransferase |
| 9 | orf9 | 8349-8783 | Galactosyltransferase (?) |
| 10 | rfp | 1134 bp (on small plasmid | Galactosyltransferase |

Summary

Referring to Table 1 and FIGS. 1-3:

1. The O-Ps biosynthetic determinants from *Shigella dysenteriae* serotype 1 strain 1617 were cloned from both the chromosome (i.e., rfb locus) and a small 9 kb plasmid (i.e., the rfp gene).

2. The separate rfb locus (GenBank accession: AY585348) and rfP region (GenBank accession: AY763519) covering ~11 kb total DNA were sequenced entirely and revealed a total of 10 ORFs apparently necessary for O-Ps biosynthesis.

3. A low copy pGB2 vector containing both the rfb and rfp loci in tandem linkage was constructed (i.e., pGB2-Sd1) and found to express *Shigella dysenteriae* serotype 1 O-Ps antigen.

4. Requirements for sugar linkage in the final O-Ps structure of *Shigella dysenteriae* serotype 1 are proposed.

5. We anticipate that use of this cloned antigen locus in a live, attenuated *Salmonella* delivery system will lead to a safe, oral vaccine for protection against this severe form of shigellosis.

Part 1

In one embodiment, the invention comprises a prokaryotic microorganism. Preferably, the prokaryotic microorganism is an attenuated strain of *Salmonella*. However, alternatively other prokaryotic microorganisms such as attenuated strains of *Escherichia coli, Shigella, Yersinia, Lactobacillus, Mycobacteria, Listeria* or *Vibrio* could be used. Examples of suitable strains of microorganisms include *Salmonella typhimurium, Salmonella typhi, Salmonella dublin, Salmonella enteretidis, Escherichia coli, Shigella flexnieri, Shigella sonnet, Vibrio cholera*, and *Mycobacterium bovis* (BCG).

In a preferred embodiment the prokaryotic microorganism is *Salmonella typhi* Ty21 a. Vivotif® Typhoid Vaccine Live Oral Ty21a is a live attenuated vaccine for oral administration only. The vaccine contains the attenuated strain *Salmonella typhi* Ty21a. (Germanier et al. 1975 *J. Infect. Dis.* 131:553-558). It is manufactured by Bema Biotech Ltd. Berne, Switzerland. *Salmonella typhi* Ty21a is also described in U.S. Pat. No. 3,856,935.

As mentioned above, the attenuated strain of the prokaryotic microorganism is transformed with a nucleic acid encoding one or more O-Ps genes. The inventors found for the first time that, when this nucleic acid is expressed in the microorganisms, core-linked O-Ps LPS are generated.

In a further aspect, the present invention provides a composition comprising one or more of above attenuated prokaryotic microorganisms, optionally in combination with a pharmaceutically or physiologically acceptable carrier. Preferably, the composition is a vaccine, especially a vaccine for mucosal immunization, e.g., for administration via the oral, rectal, nasal, vaginal or genital routes. Advantageously, for prophylactic vaccination, the composition comprises one or more strains of *Salmonella* expressing a plurality of different O-Ps genes.

In a further aspect, the present invention provides an attenuated strain of a prokaryotic microorganism described above for use as a medicament, especially as a vaccine.

In a further aspect, the present invention provides the use of an attenuated strain of a prokaryotic microorganism transformed with nucleic acid encoding enzymes for O-Ps synthesis, wherein the O-Ps are produced in the microorganism, in the preparation of a medicament for the prophylactic or therapeutic treatment of bacterial infection.

Generally, the microorganisms or O-Ps according to the present invention are provided in an isolated and/or purified form, i.e., substantially pure. This may include being in a composition where it represents at least about 90% active ingredient, more preferably at least about 95%, more preferably at least about 98%. Such a composition may, however, include inert carrier materials or other pharmaceutically and physiologically acceptable excipients. A composition according to the present invention may include in addition to the microorganisms or O-Ps as disclosed, one or more other active ingredients for therapeutic or prophylactic use, such as an adjuvant.

The compositions of the present invention are preferably given to an individual in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g., decisions on dosage etc, is within the responsibility of general practitioners and other medical doctors.

A composition may be administered alone or in combination with other treatments, either simultaneously or sequentially dependent upon the condition to be treated.

Pharmaceutical compositions according to the present invention, and for use in accordance with the present invention, may include, in addition to active ingredient, a pharmaceutically or physiologically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration.

Examples of techniques and protocols mentioned above can be found in Remington's Pharmaceutical Sciences, 16th edition, Osol, A. (ed), 1980.

The invention further relates to the identification and sequencing of 9 ORFs in the rfb locus (GenBank accession number: AY585348) and an ORF in the rfb locus (GenBank accession number: AY763519). These genes may be present in whole or in part in the vaccine strains described herein.

Accordingly, the present invention relates to vaccine strains further characterized by the presence of heterologous genes or a set of heterologous genes coding for O-Ps.

In a preferred embodiment of the vaccine strains, the heterologous gene(s) is (are) present either on a plasmid vector or stably integrated into the chromosome of said strain at a defined integration site which is to be nonessential for inducing a protective immune response by the carrier strain.

In a preferred embodiment, the heterologous genes of the invention, including all 9 ORFs from the rfb locus and the ORF from rfp, are present on a plasmid derived from pGB2 (Churchward et al. 1984 Gene 31:165-171). In another embodiment, the ninth ORF from rfb is not present, because it is not essential for O-Ps biosynthesis.

The ORFs may be under the control of the cognate promoter or other non-cognate promoters. The rfb genes may be separated and present on separate polynucleotide molecules under the control of different promoters, or on the same polynucleotide molecule in any order.

Alternatively, the above vaccine strains contain the rfbB, rfbC, and rfbA and/or any additional gene(s) necessary for the synthesis of complete core-linked O-antigen LPS which are integrated in tandem into a single chromosomal site or independently integrated into individual sites, or cloned into a plasmid or plasmids.

Such vaccine strains allow expression of heterologous O-Ps which is covalently coupled to a heterologous LPS core region, which, preferably, exhibits a degree of polymerization essentially indistinguishable from that of native LPS produced by the enteric pathogen. Such vaccine strains can, if desired, modified in such a way that they are deficient in the synthesis of homologous LPS core.

The invention also relates to a live vaccine comprising the above vaccine strain and optionally a pharmaceutically or physiologically acceptable carrier and/or a buffer for neutralizing gastric acidity and/or a system for delivering said vaccine in a viable state to the intestinal tract.

Said vaccine comprises an immuno-protective or -therapeutic and non-toxic amount of said vaccine strain. Suitable amounts can be determined by the person skilled in the art and are typically $10^7$ to $10^9$ bacteria.

Pharmaceutically and physiologically acceptable carriers, suitable neutralizing buffers, and suitable delivering systems can be selected by the person skilled in the art.

In a preferred embodiment said live vaccine is used for immunization against gram-negative enteric pathogens.

The mode of administration of the vaccines of the present invention may be any suitable route which delivers an immunoprotective or immunotherapeutic amount of the vaccine to the subject. However, the vaccine is preferably administered orally or intranasally.

The invention also relates to the use of the above vaccine strains for the preparation of a live vaccine for immunization against gram-negative enteric pathogens. For such use the vaccine strains are combined with the carriers, buffers and/or delivery systems described above.

The invention also provides polypeptides and corresponding polynucleotides required for synthesis of core linked O-specific polysaccharide. The invention includes both naturally occurring and unnaturally occurring polynucleotides and polypeptide products thereof. Naturally occurring O antigen biosynthesis products include distinct gene and polypeptide species as well as corresponding species homologs expressed in organisms other than *Shigella dysenteriae* serotype 1 strains. Non-naturally occurring O antigen biosynthesis products include variants of the naturally occurring products such as analogs and O antigen biosynthesis products which include covalent modifications. In a preferred embodiment, the invention provides O antigen biosynthesis polynucleotides comprising the sequences set forth in SEQ ID NOs: 1 and 2 and species homologs thereof, and polypeptides having amino acids sequences encoded by the polynucleotides.

The present invention provides novel purified and isolated *Shigella dysenteriae* serotype 1 polynucleotides (e.g., DNA sequences and RNA transcripts, both sense and complementary antisense strands) encoding the bacterial O antigen biosynthesis gene products. DNA sequences of the invention include genomic and cDNA sequences as well as wholly or partially chemically synthesized DNA sequences. Genomic DNA of the invention comprises the protein coding region for a polypeptide of the invention and includes variants that may be found in other bacterial strains of the same species. "Synthesized," as used herein and is understood in the art, refers to purely chemical, as opposed to enzymatic, methods for producing polynucleotides. "Wholly" synthesized DNA sequences are therefore produced entirely by chemical means, and "partially" synthesized DNAs embrace those wherein only portions of the resulting DNA were produced by chemical means. Preferred DNA sequences encoding *Shigella dysenteriae* serotype 1 O antigen biosynthesis gene products are set out in SEQ ID NOs: 1 and 2, and species homologs thereof.

The worker of skill in the art will readily appreciate that the preferred DNA of the invention comprises a double-stranded molecule, for example, molecules having the sequences set forth in SEQ ID NOs: 1 and 2 and species homologs thereof, along with the complementary molecule (the "non-coding strand" or "complement") having a sequence deducible from the sequence of SEQ ID NOs: 1 and 2, according to Watson-Crick basepairing rules for DNA. Also preferred are polynucleotides encoding the gene products encoded by any one of the polynucleotides set out in SEQ ID NOs: 1 and 2 and species homologs thereof.

The invention also embraces DNA sequences encoding bacterial gene products which hybridize under moderately to highly stringent conditions to the non-coding strand, or complement, of any one of the polynucleotides set out in SEQ ID NOs: 1 and 2, and species homologs thereof. DNA sequences encoding O antigen biosynthesis polypeptides which would hybridize thereto but for the degeneracy of the genetic code are contemplated by the invention. Exemplary high stringency conditions include a final wash in buffer comprising 0.2 X SSC/0.1% SDS, at 65° C. to 75° C., while exemplary moderate stringency conditions include a final wash in buffer comprising 2 X SSC/0.1% SDS, at 35° C. to 45° C. It is understood in the art that conditions of equivalent stringency can be achieved through variation of temperature and buffer, or salt concentration as described in Ausubel, et al. (eds.), Short Protocols in Molecular Biology, John Wiley & Sons (1994), pp. 6.0.3 to 6.4.10. Modifications in hybridization conditions can be empirically determined or precisely calculated based on the length and the percentage of guanosine-cytosine (GC) base pairing of the probe. The hybridization conditions can be calculated as described in Sambrook, et al., (eds.), Molecular Cloning: A Laboratory Manual, Cold Spring Harbor Laboratory Press: Cold Spring Harbor, N.Y. (1989), pp. 9.47 to 9.51.

Autonomously replicating recombinant expression constructions such as plasmid and viral DNA vectors incorporating O antigen biosynthesis gene sequences are also provided. Expression constructs wherein O antigen biosynthesis polypeptide-encoding polynucleotides are operatively linked to an endogenous or exogenous expression control DNA sequence and a transcription terminator are also provided. The O antigen biosynthesis genes may be cloned by PCR, using *Shigella dysenteriae* serotype 1 genomic DNA as the template. For ease of inserting the gene into expression vectors, PCR primers are chosen so that the PCR-amplified gene has a restriction enzyme site at the 5' end preceding the initiation codon ATG, and a restriction enzyme site at the 3' end after the termination codon TAG, TGA or TAA. If desirable, the codons in the gene are changed, without changing the amino acids, according to *E. coli* codon preference described by Grosjean and Fiers, 1982 *Gene* 18: 199-209; and Konigsberg and Godson, 1983 *PNAS* USA 80:687-691. Optimization of codon usage may lead to an increase in the expression of the gene product when produced in *E. coli*. If the gene product is to be produced extracellularly, either in the periplasm of *E. coli* or other bacteria, or into the cell culture medium, the gene is cloned without its initiation codon and placed into an expression vector behind a signal sequence.

According to another aspect of the invention, host cells are provided, including procaryotic and eukaryotic cells, either stably or transiently transformed, transfected, or electroporated with polynucleotide sequences of the invention in a manner which permits expression of O antigen biosynthesis polypeptides of the invention. Expression systems of the invention include bacterial, yeast, fungal, viral, invertebrate, and mammalian cells systems. Host cells of the invention are a valuable source of immunogen for development of antibodies specifically immunoreactive with the O antigen biosynthesis gene product. Host cells of the invention are conspicuously useful in methods for large scale production of O antigen biosynthesis polypeptides wherein the cells are grown in a suitable culture medium and the desired polypeptide products are isolated from the cells or from the medium in which the cells are grown by, for example, immunoaffinity purification or any of the multitude of purification techniques well known and routinely practiced in the art. Any suitable host cell may be used for expression of the gene product, such as *E. coli*, other bacteria, including *P. multocida, Bacillus* and *S. aureus*, yeast, including *Pichia pastoris* and *Saccharomyces cerevisiae*, insect cells, or mammalian cells, including CHO cells, utilizing suitable vectors known in the art. Proteins may be produced directly or fused to a peptide or polypeptide, and either intracellularly or extracellularly by secretion into the periplasmic space of a bacterial cell or into the cell culture medium. Secretion of a protein requires a signal peptide (also known as pre-sequence); a number of signal sequences from prokaryotes and eukaryotes are known to function for the secretion of recombinant proteins. During the protein secretion process, the signal peptide is removed by signal peptidase to yield the mature protein.

To simplify the protein purification process, a purification tag may be added either at the 5' or 3' end of the gene coding sequence. Commonly used purification tags include a stretch of six histidine residues (U.S. Pat. Nos. 5,284,933 and 5,310,663), a streptavidinaffinity tag described by Schmidt and Skerra, (1993 Protein Engineering 6:109-122), a FLAG peptide (Hopp et al. 1988 Biotechnology 6:1205-1210), glutathione 5-transferase (Smith and Johnson, 1988 Gene 67:31-40), and thioredoxin (LaVallie et at. 1993 Bio/Technology 11:187-193). To remove these peptide or polypeptides, a proteolytic cleavage recognition site may be inserted at the fusion junction. Commonly used proteases are factor Xa, thrombin, and enterokinase.

The invention also provides purified and isolated *Shigella dysenteriae* serotype 1 O antigen biosynthesis polypeptides encoded by a polynucleotide of the invention. Presently preferred are polypeptides comprising the amino acid sequences encoded by any one of the polynucleotides set out in SEQ ID NOs: 1 and 2, and species homologs thereof. The invention embraces O antigen biosynthesis polypeptides encoded by a DNA selected from the group consisting of:

a) the DNA sequence set out in any one of SEQ ID NOs: 1 and 2 and species homologs thereof;

b) DNA molecules encoding *Shigella dysenteriae* serotype 1 polypeptides encoded by any one of SEQ ID NOs: 1 and 2, and species homologs thereof; and c) a DNA molecule encoding a O antigen biosynthesis gene product that hybridizes under moderately stringent conditions to the DNA of (a) or (b).

The invention also embraces polypeptides that have at least about 99%, at least about 95%, at least about 90%, at least about 85%, at least about 80%, at least about 75%, at least about 70%, at least about 65%, at least about 60%, at least about 55%, and at least about 50% identity and/or homology to the preferred polypeptides of the invention. Percent amino acid sequence "identity" with respect to the preferred polypeptides of the invention is defined herein as the percentage of amino acid residues in the candidate sequence that are identical with the residues in the O antigen biosynthesis gene product sequence after aligning both sequences and introducing gaps, if necessary, to achieve the maximum percent sequence identity, and not considering any conservative substitutions as part of the sequence identity. Percent sequence "homology" with respect to the preferred polypeptides of the invention is defined herein as the percentage of amino acid residues in the candidate sequence that are identical with the residues in one of the O antigen biosynthesis polypeptide sequences after aligning the sequences and introducing gaps, if necessary, to achieve the maximum percent sequence identity, and also considering any conservative substitutions as part of the sequence identity. Conservative substitutions can be defined as set out in Tables A and B.

TABLE A

| Conservative Substitutions I | | |
|---|---|---|
| SIDE CHAIN | CHARACTERISTIC | AMINO ACID |
| Aliphatic | Non-polar | G, A, P |
| | | I, L, V |
| | Polar-uncharged | C, S, T, M |
| | | N, Q |
| | Polar-charged | D, E |
| | | K, R |
| Aromatic | | H, F, W, Y |
| Other | | N, Q, D, E |

Polypeptides of the invention may be isolated from natural bacterial cell sources or may be chemically synthesized, but are preferably produced by recombinant procedures involving host cells of the invention. O antigen biosynthesis gene products of the invention may be full length polypeptides, biologically active fragments, or variants thereof which retain specific biological or immunological activity. Variants may comprise O antigen biosynthesis polypeptide analogs wherein one or more of the specified (i.e., naturally encoded) amino acids is deleted or replaced or wherein one or more non-specified amino acids are added: (1) without loss of one or more of the biological activities or immunological characteristics specific for the O antigen biosynthesis gene product; or (2) with specific disablement of a particular biological activity of the O antigen biosynthesis gene product. Deletion variants contemplated also include fragments lacking portions of the polypeptide not essential for biological activity, and insertion variants include fusion polypeptides in which the wild-type polypeptide or fragment thereof have been fused to another polypeptide.

Variant O antigen biosynthesis polypeptides include those wherein conservative substitutions have been introduced by modification of polynucleotides encoding polypeptides of the invention. Conservative substitutions are recognized in the art to classify amino acids according to their related physical properties and can be defined as set out in Table A (from WO97/09433, page 10). Alternatively, conservative amino acids can be grouped as defined in Lehninger, (Biochemistry, Second Edition; W.H. Freeman & Co. 1975, pp. 71-77) as set out in Table B.

TABLE B

| Conservative Substitutions II | |
|---|---|
| SIDE CHAIN CHARACTERISTIC | AMINO ACID |
| Non-polar (hydrophobic) | |
| A. Aliphatic: | A, L, I, V, P |
| B. Aromatic: | F, W |
| C. Sulfur-containing: | M |
| D. Borderline: | G |
| Uncharged-polar | |
| A. Hydroxyl: | S, T, Y |
| B. Amides: | N, Q |
| C. Sulfhydryl: | C |
| D. Borderline: | G |
| Positively Charged (Basic): | K, R, H |
| Negatively Charged (Acidic): | D, E |

Variant O antigen biosynthesis products of the invention include mature O antigen biosynthesis gene products, i.e., wherein leader or signal sequences are removed, having additional amino terminal residues. O antigen biosynthesis gene products having an additional methionine residue at position −1 are contemplated, as are O antigen biosynthesis products having additional methionine and lysine residues at positions −2 and −1. Variants of these types are particularly useful for recombinant protein production in bacterial cell types. Variants of the invention also include gene products wherein amino terminal sequences derived from other proteins have been introduced, as well as variants comprising amino terminal sequences that are not found in naturally occurring proteins.

The invention also embraces variant polypeptides having additional amino acid residues which result from use of specific expression systems. For example, use of commercially available vectors that express a desired polypeptide as fusion protein with glutathione-S-transferase (GST) provide the desired polypeptide having an additional glycine residue at position −1 following cleavage of the GST component from the desired polypeptide. Variants which result from expression using other vector systems are also contemplated.

Also comprehended by the present invention are antibodies (e.g., monoclonal and polyclonal antibodies, single chain antibodies, chimeric antibodies, humanized, human, and CDR-grafted antibodies, including compounds which include CDR sequences which specifically recognize a polypeptide of the invention) and other binding proteins specific for O antigen biosynthesis gene products or fragments thereof. The term "specific for" indicates that the variable regions of the antibodies of the invention recognize and bind a O antigen biosynthesis polypeptide exclusively (i.e., are able to distinguish a single O antigen biosynthesis polypeptides from related O antigen biosynthesis polypeptides despite sequence identity, homology, or similarity found in the family of polypeptides), but may also interact with other proteins (for example, *S. aureus* protein A or other antibodies in ELISA techniques) through interactions with sequences outside the variable region of the antibodies, and in particular, in the constant region of the molecule. Screening assays to determine binding specificity of an antibody of the invention are well known and routinely practiced in the art. For a comprehensive discussion of such assays, see Harlow et al. (eds.), Antibodies A Laboratory Manual; Cold Spring Harbor Laboratory; Cold Spring Harbor, N.Y. (1988), Chapter 6. Antibodies that recognize and bind fragments of the O antigen biosynthesis polypeptides of the invention are also contemplated, provided that the antibodies are first and foremost specific for, as defined above, a O antigen biosynthesis polypeptide of the invention from which the fragment was derived.

Part II

Molecular Characterization of Genes for *Shigella dysenteriae* Serotype 1 O-Antigen and Expression in a Live *Salmonella* Vaccine Vector Abstract

*Shigella dysenteriae* serotype 1, a bioterrorist threat agent, causes the most severe form of shigellosis and is typically associated with high mortality rates, especially in developing countries. This severe disease is due largely to Shiga-toxin-induced hemorrhagic colitis, plus hemolytic uremic syndrome in children. The lipopolysaccharide of *Shigella dysenteriae* serotype 1 is essential for virulence, and there is substantial evidence that antibodies against *Shigella* O-specific polysaccharide (O-Ps) are protective to the host. Thus, there is considerable interest in the development of an O-Ps-based vaccine to protect against *Shigella dysenteriae* serotype 1. Previous studies have shown that the genetic determinants for the production of O-Ps antigen in *Shigella dysenteriae* serotype 1 are uniquely distributed on the chromosome (i.e., rfb genes) and on a small 9 kb plasmid (i.e., the rfp gene). In the current studies, the multi-ORF rfb gene cluster and the rfp gene with their cognate promoter regions have been amplified by PCR from *Shigella dysenteriae* serotype 1 strain 1617. The two interrelated biosynthetic gene loci were then cloned and sequenced. Sequencing studies revealed 9 ORFs located in the amplified 9.2 kb rfb region. Further deletion studies showed that only eight ORFs in the rfb region are necessary, together with rfp, for *Shigella dysenteriae* serotype 1 O-Ps biosynthesis. A linked rfb-rfp gene region cassette was constructed and cloned into the low copy plasmid pGB2, resulting in the recombinant plasmid designated pGB2-Sd1. When introduced by transformation into either *Salmonella enterica* serovar *Typhi* Ty21a or *E. coli* K-12, pGB2-Sd1 directed the formation of surface-expressed, core-linked *Shigella dysenteriae* serotype 1 O-specific lipopolysaccharide. Silver stain and Western immunoblotting analyses showed that the distribution of O repeat units in *S. typhi* or *E. coli* K-12 was similar when compared with the pattern observed for the wild type strain 1617 of *Shigella dysenteriae* serotype 1. In addition, a proposed biopathway, based upon ORF sequence homologies to known genes, was developed. We anticipate that the insertion of these jointly-cloned, O-Ps biosynthetic loci in a live, bacterial vaccine delivery system, such as attenuated *S. typhi*, will produce a safe, oral vaccine for protection against this severe form of shigellosis.

Introduction

Bacillary dysentery is a severe inflammation of the colon caused classically by the entero-invasive bacterial genus *Shigella*. The estimated number of bacillary dysentery infections worldwide is over 200 million annually, with more than 650,000 associated deaths globally each year (Kotloff, K. L. et al. 1999 *Bull World Health Organ* 77:651-66). Shigellosis, especially in developing countries, is predominantly a disease of childhood. More than half of the cases occur in children less than 5 years of age, Shigellosis is highly transmissible due to the very low infective dose of *Shigella* (i.e., <100 bacteria) and bacterial spread via the fecal-oral route (DuPont, H. L. et al. 1989 *J Infect Dis* 159:1126-1128). *Shigella dysenteriae* serotype 1 (Shiga 1) is the primary causative agent of epidemic outbreaks of severe bacillary dysentery which is associated with increased mortality. Due to the presence of high levels of Shiga toxin produced by *Shigella dysenteriae* serotype 1 strains, infections are more severe than those caused by other *Shigella* spps. and are often characterized by serious complications (e.g., hemolytic-uremic syndrome, hemorrhagic colitis, sepsis, and purpura) (Levine, M. M. 1982 *Med Clin North Am* 66:623-638). In addition, the emergence of strains resistant to multiple antibiotics makes therapeutic treatment difficult, particularly in developing countries, and emphasizes the need for vaccines in disease control. For these reasons, the World Health Organization (WHO) has given high priority to the development of a protective vaccine against *Shigella dysenteriae* serotype 1 (Oberhelman, R. A. et al. 1991 *Bull World Health Organ* 69:667-676). The increased concern for the potential use of this food- and water-borne pathogen of high morbidity and mortality as a bioterrorist agent has recently amplified the interest in developing an anti-Shiga 1 vaccine.

Protective immunity against shigellosis is serotype-specific and correlates with stimulation of both systemic and local intestinal immunity against the O-specific surface lipopolysaccharide (LPS) (Viret, J. F. et al. 1994 *Biologicals* 22:361-372; Winsor, D. K. et al. 1988 *J Infect Dis* 158:1108-1112). Genes for *Shigella dysenteriae* serotype 1 O antigen biosynthesis are uniquely located in two unlinked gene clusters; one gene, rfp is located unusually on a 9 kb multicopy plasmid (Watanabe, H. et al. 1984 *Infect Immun* 43:391-396), and the remaining biosynthetic genes are clustered, as usual, in the rfb chromosomal locus (Hale, T. L. et al. 1984 *Infect Immun* 46:470-5; Sturm, S. et al. 1986 *Microb Pathog* 1:289-297). The O-Ps of *Shigella dysenteriae* serotype 1 consists of the repeating tetrasaccharide unit: -3)-alpha-L-Rhap (1-3)-alpha-L-Rhap (1-2)-alpha-D-Galp (1-3)-alpha D-GlcNAcp (1-core oligosaccharide. (Dmitriev, B. A. et al. 1976 *Eur J Biochem* 66:559-566; Falt, I. C. et al. 1996 *Microb Pathog* 20:11-30.)

The availability of a safe *Salmonella typhi* live, oral vaccine strain since late 1970's stimulated new research efforts with the goals of expressing protective antigens (e.g., *Shigella* O-Ps) in an *S. typhi* carrier that could be used as a hybrid vaccine (e.g., to protect against bacillary dysentery or other diseases) (Formal, S. B. et al. 1981 *Infect Immun* 34:746-50). In this initial study, the *S. typhi* Ty21a strain was employed as a delivery vector for expression of the form 1 O-Ps antigen of *S. sonnei*. However, the protection in volunteers provided by immunizing with this hybrid vaccine strain varied (Herrington, D. A. et al. 1990 *Vaccine* 8:353-357), presumably due to spontaneous, high frequency deletion of the form 1 gene region from a very large 300 kb cointegrate plasmid in vaccine strain 5076-IC (Hartman, A. B. et al. 1991 *J Clin Microbiol* 29:27-32). In more recent studies, we have constructed a refined *S. sonnei*-Ty21a bivalent vaccine strain by using the defined O antigen gene cluster cloned into a genetically stable low copy plasmid. This refined hybrid vaccine strain showed highly stable expression of form 1 antigen and following immunization it protected mice against a stringent challenge with virulent *S. sonnei* (Xu, D. Q. et al. 2002 *Infect Immun* 70:4414-23).

In a similar vaccine development approach, the rfp gene and genes of the rfb cluster of *Shigella dysenteriae* serotype 1 were introduced together into attenuated strains of *S. typhimurium* (Falt, I. C. et al. 1996 *Microb Pathog* 20:11-30), *S. typhi* (Mills, S. D. et al. 1988 *Vaccine* 6:11622), or *Shigella flexneri* (Klee, S. R. et al. 1997 *Infect Immun* 65:2112-2118)

to create vaccine candidates for protection from this *Shigella* serotype. However, the *Shigella dysenteriae* serotype 1 O-Ps antigen was expressed as core-linked in *Shigella* and in *S. typhimurium* (Falt, I. C. et al. 1996 *Microb Pathog* 20: 11-30), but was reportedly not core-linked in *S. typhi* (Mills, S. D. et al. 1988 *Vaccine* 6:116-22). In the current studies, the *Shigella dysenteriae* serotype 1 O antigen gene loci were cloned, sequenced completely and analyzed. Putative genes involved in synthesis of the tetrasaccharide O-repeating unit including L-Rhap, L-Rhap, D-Galp, and D-GlcNAcp, as well as genes for O-unit processing and polymerization were identified. The four Rfb genes involved in rhamnose biosynthesis in *Shigella dysenteriae* serotype 1 were found to be identical to those of *E. coli* 026, indicating common ancestry. In contrast to a previous report, analyses for the expression of LPS in *S. typhi* Ty21a carrying the *Shigella dysenteriae* serotype 1 O-antigen encoding rfb-rfp genes showed that the O-antigen repeat units are linked to the *Salmonella typhi* core and are envisioned as stimulating protection in mice against challenge with virulent *Shigella dysenteriae* serotype 1.

Materials and Methods

Bacterial strains, plasmids and growth conditions. The bacterial strains and plasmids utilized are described in Table 2. The wild type parent *Shigella dysenteriae* serotype 1 strain 1617 was obtained from S. B. Formal, Walter Reed Army Institute of Research (WRAIR) (Neill, R. J. et al. 1988 *J Infect Dis* 158:737-741). The strain was originally isolated from an outbreak of epidemic Shiga *bacillus* dysentery in Guatemala, Central America, in 1968 or early 1969 (Mendizabal-Morris, C A. et al. 1971 *J Trop Med Hyg* 20:927-933). The isolated strain 1617 was lyophilized and has been stored in sealed glass ampules. This strain is sensitive to ampicillin, spectinomycin, streptomycin, tetracycline, chloramphenicol, and kanamycin. Strain 1617 was used to obtain the O-antigen biosynthetic genes and as a positive control for LPS expression analyses. Studies of plasmid-based *Shigella dysenteriae* serotype 1 LPS expression were performed in *Escherichia coli* DH5α, and *Salmonella enterica* serovar *Typhi* strain Ty21a. *Shigella dysenteriae* serotype 1 strain 60R (rough strain, $Spc^r$ which has lost the small plasmid carrying rfp) was used as an LPS-negative control.

TABLE 2

| Bacterial strains and plasmids | | |
|---|---|---|
| Strain or plasmid | Genotype or description | Reference or source |
| *E. coli* DH5α | supE44 hsdR17 recA1 endA1 gyrA96 thi-1 relA1 (*E. coli* K12-origined) | Sambrook, J. et al. 1989 Molecular cloning: a laboratory manual, $2^{nd}$ ed. Cold Spring Harbor Laboratory Press, Cold Spring Harbor, N.Y. |
| *E. coli* XL 1-blue | supE44 hsdR17 rec A1 endA1 gyrA96 thi-1 relA1 lac[F' proAB lacIq ZM15Tn10 ($Tet^r$)] (K12-DH5α-origined) | Sambrook, J. et al. 1989 (supra) |
| *E. coli* TOP10F' | F' {$lacI^q$ Tn10 ($Tet^r$} mcrA Δ(mmr-hsdRMS-mcrBC) φ801acZ ΔM15 Δ lacX74 recA1araD139 Δ(ara-leu)7697 galU galK rpsL ($Str^r$) endA1 nupG | Invitrogen |
| *Salmonella enterica* | serovar Typhi Ty21a galE ilvD viaB (Vi) h2S | Germanier, R. and E. Furer 1975 *J Infect Dis* 131: 553-558 |
| *Shigella dysenteriae* serotype 1 | 1617, virulent | S. Formal (Neill, R. J. et al. 1988 *J Infect Dis* 158: 737-741) |
| *Shigella dysenteriae* serotype 1 60R | rough LPS mutant missing rfp plasmid | S. Formal (Neill, R. J. et al. 1988 *J Infect Dis* 158: 737-741) |
| Plasmid | | |
| pGB2 | pSC101 derivative, low copy plasmid; $Sm^r$, $Spc^r$ | Churchward, G. et al. 1984 *Gene* 31: 165-171 |
| pCR2.1-TOPO | PCR TA cloning vector, pUC origin, $Amp^r$ $Kan^r$ | Invitrogen |
| pXK-Tp | pCR2.1-TOPO containing rfp gene of strain 1617, $Amp^r$ $Kan^r$ | this study |
| pXK-Bp56 | pGB2 containing rfp gene of strain 1617, $Spc^r$ | this study |
| pXK-T4 | pCR2.1-TOPO containing rfb gene cluster, $Amp^r$ $Kan^r$ | this study |
| pGB2-Sd1 | pGB2 containing *S. dysenteriae* rfb-rfp gene cassette, $Spc^r$ | this study |

Plasmids pGB2 (which is derived from plasmid pSC101) and pCR2.1-TOPO (Invitrogen) were used for cloning and subcloning. Bacterial strains were grown at 37° C. in Luria-Bertani (LB) broth or on LB agar (Difco). *S. enterica* serovar *Typhi* Ty21a strain was grown in SOB (soy broth) medium (Difco). Plasmid-containing strains were selected in medium containing ampicillin (Amp; 100 μg/ml for *E. coli* and 25 μg/ml for *S. enterica* serovar *Typhi* or spectinomycin (Spc; 100 μg for *E. coli,* 50 μg/ml for *S. enterica* serovar *Typhi* Ty21a).

PCR and DNA cloning. Unless otherwise noted all DNA manipulations were performed essentially by following the procedures outlined by Sambrook et al. (Sambrook, J. et al. 1989 Molecular cloning: a laboratory manual, 2nd ed. Cold Spring Harbor Laboratory Press, Cold Spring Harbor, N.Y.) or by following instructions provided with various commercially available reagents and kits, including a genomic DNA purification kit, plasmid purification kits and PCR products purification kits (Promega, Madison Wis.). Restriction enzymes (Roche) were used with the supplied buffers. Plasmid electroporation was performed with a Gene Pulser (Bio-Rad). All PCR reactions were conducted with ExTaq or LA-Taq (Takara Co).

Genomic DNA of *Shigella dysenteriae* serotype 1 strain 1617, isolated with a genomic DNA purification kit, was used as a PCR template to generate the 9.2 kb DNA fragment containing the rfb locus. A 1.6 kb DNA fragment containing the rfp gene was synthesized by PCR from *Shigella dysenteriae* serotype 1 strain 1617 genomic template material-treated by boiling. The PCR products were used for sequencing studies and for construction of the rfb-rfp linked gene region cassette. Sequencing templates included PCR products from 1.6 kb to 9.2 kb in Size.

O-Ps expression analyses. Slide agglutination was performed with rabbit antisera against *Shigella dysenteriae* serotype 1 (B-D Co., Sparks, Md. USA). For immunoblotting, *Salmonella, Shigella*, and *E. coli* strains with or without various recombinant plasmids were grown overnight with aeration at 37° C. in LB media containing appropriate antibiotics. Bacteria were pelleted by centrifugation and were lysed in sodium dodecyl sulfate-polyacrylamide gel electrophoresis (SDS-PAGE) sample buffer containing 4% 2-mercaptoethanol. The samples were heated at 95° C. for 5 min, and treated with proteinase K for 1 hr, and LPS samples were fractionated by 16% Tris-Glycine-SDS-PAGE on a Novex mini-cell gel apparatus (Invitrogen Life Technologies) at 30 rnA until tracing dye had left the gel. For immunoblotting, LPS bands were transferred to polyvinylidene floride membranes (Schleicher & Schuell, Germany). The membranes were blocked with 5% nonfat dry milk in Tris-buffered saline (TBS: 20 mM Tris-HCl, 150 mM NaCl, pH 7.5) and were reacted with rabbit polyclonal antibodies against the 0 antigen of either *Shigella dysenteriae* serotype 1 or *Salmonella typhi* (Difco Laboratories, Michigan, USA), followed by protein A-alkaline phosphatase conjugate. The developing solution consisted of 200 mg of Fast Red TR salt and 100 mg of Naphthol NS-MX phosphate (Sigma) in 50 mM Tris buffer, pH 8.0). The silver staining analysis was performed using SilverXpress Silver Staining Kit (Invitrogen) according to the manufacturer's instructions.

DNA sequence and analysis. DNA sequencing was performed with Ready Reactions DyeDeoxy Terminator cycle sequencing kits (Applied Biosystems) and an ABI model 373A automated sequencer. The PCR products including the 9.2 kb rfb region and the 1.6 kb rfp gene region, amplified from genomic DNA of *Shigella dysenteriae* serotype 1 strain 1617, were used for sequencing and construction of the linked rfb-rfp gene cassette. Sequences were assembled and analyzed by using the Vector NTI suite 9.0 software (InforMax, Inc.). DNA homology searches were performed by using the Basic Local Alignment Search Tool (BLAST) of National Center for Biotechnology Information. Putative promoters were identified by using MacVector 6.5 (Accelrys, Burlington, Mass.). The JUMPstart sequence was found by using NIH Computational Molecular Biology software, GCG-Left Sequence Comparison Tools, and the JUMPstart sequence identified from our previous studies at an upstream region of the *S. sonnei* O antigen locus (Xu, D. Q. et al. 2002 *Infect Immun* 70:4414-23). In order to confirm the fidelity of our sequence data obtained from LA Taq PCR products, the Computational Molecular Biology software, GCG-Left Sequence Comparison Tools was also used to compare with homologous sequences from a different *Shigella dysenteriae* serotype 1 strain provided by the Sanger Sequencing Institute.

Growth curves and stability of O-antigen expression in the recombinant vaccine strain. Several studies were conducted to determine if the *Salmonella* vaccine strains carrying a rfb/rfp recombinant expression plasmid are efficient for growth and stably express the Shiga-1 O-antigen. First, growth curves of recombinant strains and control bacteria under different growth conditions were compared. *Shigella dysenteriae* serotype 1 O-antigen-specific positive colonies of Sd1-Ty21a and Sd1-*E. coli* were inoculated into LB broth with or without antibiotic. Overnight cultures of each strain were diluted to an $OD_{600}$ of approximately 0.1, and growth to the stationary phase was monitored.

Animal immunization study. We are in the process of conducting animal protection studies to confirm safety and efficacy. In another embodiment, we envision removing any antibiotic resistance gene from the final plasmid construct and inserting a different selection marker (e.g., a heavy metal ion resistance gene, such as mercury resistance gene) in place of antibiotic resistance to allow for genetic manipulations. In yet another embodiment, we envision inserting a gene encoding for the Shiga toxin B subunit, which is nontoxic but stimulates immunity to whole Shiga toxin, into the final vaccine strain. Thus, in this embodiment, the final vaccine will trigger antibodies against *Shigella dysenteriae* serotype 1 LPS and against Shiga toxin to give better protection against *Shigella dysenteriae* serotype 1, and it is envisioned as providing protection against Shiga toxin-producing *E. coli* strains to prevent the occurrence of hemolytic uremic syndrome caused by Shiga toxin-mediated damage to the kidneys.

Results

Cloning the essential *Shigella dysenteriae* serotype 1 O-Ps biosynthetic genes and construction of an O-antigen gene expression cassette. Previous studies showed that the determinants for the production of O antigen lipopolysaccharide in *Shigella dysenteriae* serotype 1 are distributed on the chromosome (i.e., rfb genes) and on a small 9-kb plasmid (FIG. 1). The DNA fragment containing the rfp gene was first synthesized by PCR from the whole cell lysate (treated by boiling) of *Shigella dysenteriae* serotype 1 strain 1617 with the two primers listed below and based upon the previously published DNA sequence (GenBank Accession #: M96064): dy5: ttatttccagactccagctgtcattatg (SEQ ID NO: 13); dy6: ccatcgatattggctgggtaaggtcat (SEQ ID NO: 14).

The 1.6 kb PCR fragment was cloned into the pCR 2.1-TOPO cloning vector (Invitrogen). The resulting TOPO-rfp recombinant plasmid, designated pXK-Tp, was digested with EcoRI, then the EcoRI fragment containing the rfp gene was cloned into the EcoRI site of the low copy plasmid pGB2. The resulting pGB2-rfp recombinant plasmid was designated pXK-Bp56.

The large DNA fragment containing the 9.2 kb rfb gene cluster was amplified from *Shigella dysenteriae* serotype 1 genomic DNA directly by using LA Taq polymerase (Takara) cocktail that combines the proven performance of Taq polymerase with an efficient 3'-5' exonuclease activity for increased proofreading fidelity. The primers used in this amplification are: SalI-N: cgtatgtcgactgagctctctgaatactctgtcatccagaccaaa (SEQ ID NO: 15) (ref. to GenBank Accession #: AF529080) (a Sail restriction site is created); BamHI-C: tatcagcttttcactcaactcggcggatccgccctcatac (SEQ ID NO: 16) (ref. to GenBank Accession #: L07293) (a BamHI-C restriction site is created).

Using BLAST, we found that one of four genes which encodes enzymes involved in rhamnose biosynthesis of *E. coli O*26 strain has extensive homology with a gene (rfbD) of *Shigella dysenteriae* serotype 1 which has predicted involvement in rhamnose biosynthesis. In order to identify a potential primer binding site adjacent to the N-terminal region of the rfb gene cluster of *Shigella dysenteriae* serotype 1, a series of primers recognizing the N-terminal sequence adjacent to the O-antigen gene cluster of *E. coli* O26 were synthesized. We successfully produced a 9.2 kb DNA fragment by PCR using a primer (i.e., SalI-N) synthesized from the N-terminus of the O-antigen gene cluster of *E. coli* O26 and another primer (i.e., BamHI-C) synthesized from the previously defined C-terminal region adjacent to the rfb gene cluster of *Shigella dysenteriae* serotype 1 and using genomic DNA of *Shigella dysenteriae* serotype 1 1617 as a template. Previous studies indicated that this 9.2 kb DNA fragment contained all essential ORFs of the rfb gene cluster.

The 9.2 kb PCR DNA fragment containing the rfb gene locus was first cloned into the pCR 2.I-TOPO cloning vector (Invitrogen), resulting in plasmid pXK-T4. In order to combine this rfb gene cluster with the cloned rfp gene, plasmid pXK-T4 was digested with BamHI and SalI, and the 9.2 kb BamHI-SalI fragment was cloned into plasmid pXK-Bp56, which had been cleaved with BamHI and SalI, to produce the linked rfb-rfp gene expression cassette. The resulting new recombinant low copy pGB-2 derivative plasmid was designated pGB2-Sd1 (FIG. 2). As shown in FIG. 2, the rfp gene encoding galactosyltransferase is located downstream of the rfb gene cluster and both contain their cognate promoter regions. After pGB2-Sd1 electroporation into *E. coli* or *S. typhi*, colonies that express *Shigella dysenteriae* serotype 1 O-antigen were identified by colony immunoblotting with Shiga 1-specific antiserum.

Expression of *Shigella dysenteriae* serotype 1 O-antigen in *Salmonella typhi* vaccine strain Ty21a. Plasmid pGB2-Sd1 was transferred by electroporation into *S. enterica* serovar Typhi Ty21a. Resulting electroporants were characterized by colony immunoblot for *Shigella dysenteriae* serotype 1 O-antigen expression. All colonies showed strong positive reaction by colony immunoblot screening, and all selected Ty21a (pGB2-Sd1) colonies directed expression of Shiga 1 O-antigen as determined by slide agglutination with *Shigella dysenteriae* serotype 1-specific antiserum.

Plasmid-based expression of *Shigella dysenteriae* serotype 1 O-antigen in each host was further examined by SDS-PAGE followed by silver staining and Western immunoblotting with *Shigella dysenteriae* serotype 1-specific antisera. LPS from wild type *Shigella dysenteriae* serotype 1 strain 1617 gave a typical O-antigen ladder pattern with the predominant chain length of 17 to 21 O units as detected by both silver stain or immunoblotting (FIGS. 4A and B).

Silver stain analyses of lipopolysaccharide from various strains (FIG. 4A) revealed a series of prominent protein bands that were resistant to protease K digestion. Despite the presence of these interfering bands, several observations could be made. The control rough *E. coli* K12 carrying the empty pGB2 plasmid vector (lane pGB2.*E. coli*) as well as the *Shigella dysenteriae* serotype 1 60R rough strain (lane Sd1 60R) showed no evidence of LPS ladders, as expected. A faint LPS ladder pattern was seen with the wild type *Shigella dysenteriae* serotype 1 1617 strain (lane Sd1.1617), but was obscured by heavy protein bands in the bottom half of the gel. A similar Shiga 1 ladder pattern was observed more clearly in the *E. coli* or Ty21a strains carrying pGB2-Sd1 (lanes Sd1.*E. coli* and Sd1.Ty21a, respectively). *S. typhi* Ty21a alone showed the typical repeats of the 9, 12 ladder pattern of this serovar (lane *Typhi* Ty21a).

Figure 4B:
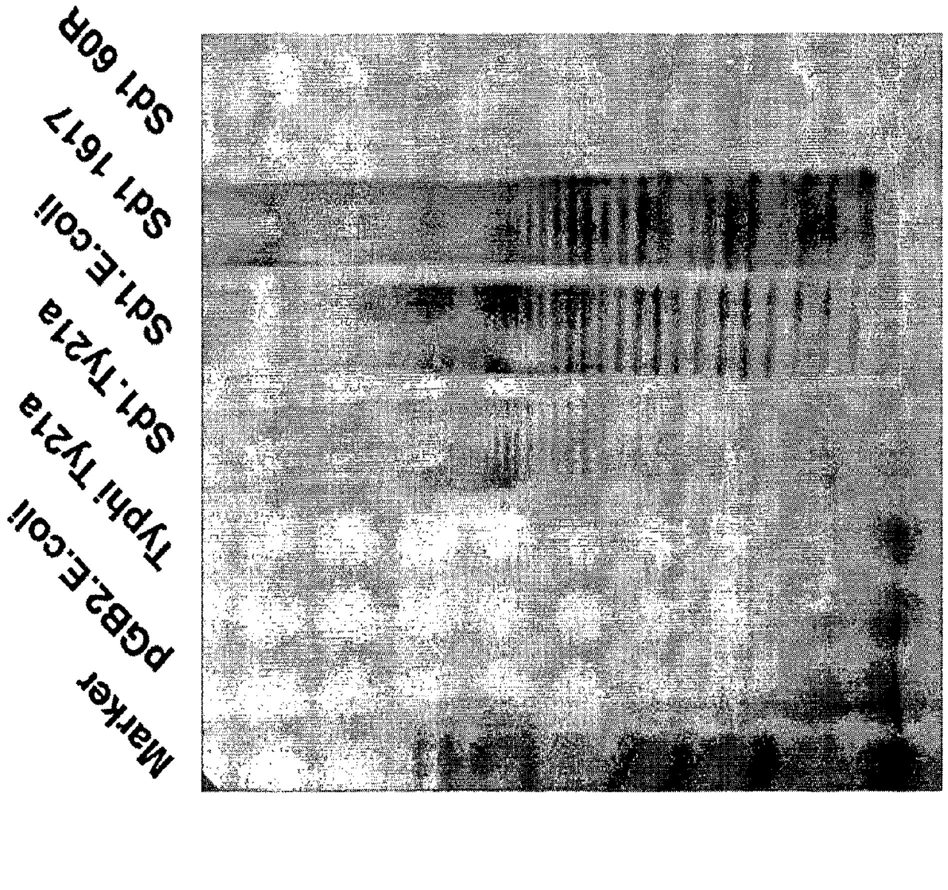

As shown in FIG. 4B, anti-*Shigella dysenteriae* serotype 1 O-antigen reactive material was not detected with *Shigella dysenteriae* serotype 1 rough strain 60R (lane Sd1 60R), rough *E. coli* K-12 carrying pGB-2 (lane pGB-2.*E. coli*) or *S. typhi* Ty21a alone (lane Sd1.Ty21a). However, recipient *S. typhi* Ty21a or *E. coli* strains carrying pGB2-Sd1 (lanes Sd1.Ty21a and Sd1.*E. coli*) showed typical LPS patterns like that seen with the *Shigella dysenteriae* serotype 1 wild type strain (lane Sd1.1617).

In this study, the *S. enterica* serovar Typhi Ty21a-bearing pGB2-Sd1 clearly exhibited the typical *Shigella dysenteriae* serotype 1-specific O-antigen LPS ladder. In contrast to the findings reported earlier, the *Shigella dysenteriae* serotype 1 O-Ps in vaccine strain Ty21a showed a core-linked LPS pattern.

Sequence analysis and a proposed biopathway for *Shigella dysenteriae* serotype 1 O-antigen synthesis. A contiguous segment of about 9.2 kb (rfb/rfc region) (GenBank # AY585348) and a 1.6 kb (rfp fragment) (GenBank #AY763519) were sequenced to characterize the *Shigella dysenteriae* serotype 1 O-antigen biosynthetic genes. Primary analysis of the 9.2 kb sequence revealed 9 open reading frames (ORFs); the last open reading frame (orf9) was identified as a small protein coding sequence. In order to demonstrate whether orf9 is essential for Shiga 1 O-antigen biosynthesis, plasmid pGB2-Sd1 was subjected to digestion with SspBI and BstXI (which are uniquely located in the middle of orf 9), followed by religation. The new construct, containing a deletion of the middle of orf9, showed identical O-antigen expression compared with the original plasmid pGB2-Sd1, indicating that orf9 is not involved in O-antigen biosynthesis.

To confirm the fidelity of the resulting sequence data obtained from PCR products synthesized using LA Taq polymerase, our 9.2 kb sequence was compared with an homologous Shiga 1 rfb region available from unpublished data using GCG Molecular Comparison Program of the Sanger Sequencing Center. The results showed 99.98% identity with the Sanger sequence from *S. dysenteriae* strain M131649 (M131) and only one nucleotide change (i.e., a G to C transition at position 2450 within rfbB; accession #: AY585348). In addition, the presumed transcriptional antiterminator JUMPstart sequence: cagtggctctggtagctgtaaagccaggggcggtagcgt (SEQ ID NO: 17) was identified at by 643-680 (GenBank accession#: AY585348) of the amplified rfb region of Shiga 1 strain 1617.

The *Shigella dysenteriae* serotype 1 O antigen genes. The properties of the nine essential genes including eight ORFs from the rfb locus plus the rfp gene, summarized in Table 2, were obtained from homology searches. The putative genes involved in biosynthesis of the tetrasaccharide repeating unit: L-Rhap, L-Rhap, D-Galp, and D-GlcNAcp as well as genes for a unit processing (e.g., encoding O antigen transporter/flipase and polymerase) were identified. The genes involved in the rhamnose biopathway, rfbB, rfbC, rfbA and rfbD, (Klena, J. D. et al. 1993 *Molec Microbio*19:393-402) share 98.5, 99, 99, and 93% identity, respectively, with the rhamnose biosynthetic genes rmlB, rmlD, rmlA and rmlC of *E. coli* O26. The enzymatic working order of the four proteins in this pathway are: RfbA, RfbB, RfbC and RfbD. RfbA/RmlA is a glucose-1-phosphatate thymidylytransferase, which links Glu-1-P to a carrier nucleotide creating dTDP-glucose for further chemical transformation. RfbB/RmlB is an dTDP-D-glucose 4, 6-dehydratase, which catalyzes the second step in the rhamnose biosynthetic pathway: the dehydration of dTDP-D-glucose to form dTDP-4-keto 6-deoxy-D-glucose. RfbC/RmlC is dTDP-4-dyhydrorhamnose reductase. RfbD/RmlD is a dTDP-4-dehydrorhamnose 3, 5-epimerase, which catalyses the terminal reaction in dTDP-L-rhamnose biosynthesis, reducing the C4-keto group of dTDP-L-lyxo-6-deoxy-4-hexulose to a hydroxyl resulting in the product dTDP-L-rhamnose. RfbX is putative O antigen transporter, which belongs to the Wzx gene family involved in the export of O antigen and teichoic acid. This protein shows only 53% identity to that of *E. coli* K-12. The next Orf is rfc, which was a member of the Wzy protein family of O antigen polymerases. Wzy proteins usually have several transmembrane segments and a large periplasmic loop which interacts with the O antigen chain length determinant Cld/wzz to control O-Ps repeat unit chain length and distribution on the cell surface. There are two putative rhamnosyltransferases which are located at the end of this rfb locus. The transferase must recognize both the sugar nucleotide and the recipient polymer to which the sugar is transferred, forming a specific glycosidic linkage. There are two rhamnosyltranferases which work in tandem to link the 2 rhamnoses at the end of the O-repeat unit. We suggest that the *S. typhi* chromosomal Rfe, which is very conserved in gram-negative bacteria, is a GlcNac transferase which first adds GlcNAc to the ACL (antigen carrier lipid/acyl lipid carrier/undecaprenol phosphate). Rfp is a galactosyltransferase, which normally transfers the Gal moiety from UDP-Gal to the GluNAc-bound ACL. Following these two sugars, the 2 terminal rhamnoses are transferred to complete the tetrasaccharide O-repeat unit.

Summary

The O-Ps biosynthetic determinants from *Shigella dysenteriae* serotype 1 strain 1617 were cloned from both the chromosome (i.e., rfb locus) and a small 9 kb plasmid (i.e., the rfp gene). The separate rfb locus and ifp region covering ~11 kb total DNA were sequenced entirely. Sequencing data and genetic deletion studies in one terminal orf revealed that 8 Rib orf's and the single Rfp orf are necessary for O-Ps biosynthesis. A low copy pGB2 vector containing both the rfb and rfp loci in tandem linkage with their cognate promoters was constructed (i.e., pGB2-Sd1). This plasmid is genetically stable and promotes the expression of *Shigella dysenteriae* serotype 1 O-Ps antigen as a typical core-linked structure in both *E. coli* and *S. Typhi* recipients. Sequence comparisons revealed proposed gene functions for the 9 required Orf's that result in the biosynthesis of a tetrasaccharide repeat O-unit as well 9* as its processing, transport and linkage to core oligosaccharide. We anticipate that use of this cloned antigen locus in a live, attenuated *Salmonella* delivery system will lead to a safe, oral vaccine for protection against this severe form of shigellosis.

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

The invention claimed is:

1. *Salmonella typhi* Ty21a comprising core-linked *Shigella dysenteriae* serotype 1 O-specific polysaccharide (O-Ps) and DNA encoding O antigen biosynthesis, said DNA selected from the group consisting of:

DNA encoding variants of *Shigella dysenteriae* serotype 1 biosynthesis polypeptides encoded by any one of SEQ ID NOs: 1 and 2, wherein the variants comprise O antigen biosynthesis polypeptide analogs, wherein one or more of the specified amino acids is deleted or replaced, or wherein one or more non-specified amino acids are added without loss of biosynthesis of *Shigella dysenteriae* serotype 1 O antigen or protective immunological activity of the O antigen biosynthesis gene product, said DNA being present on a plasmid.

2. *Salmonella typhi* Ty21a comprising core-linked *Shigella dysenteriae* serotype 1 O-specific polysaccharide (O-Ps) and DNA encoding O antigen biosynthesis, said DNA selected from the group consisting of:

DNA encoding variants of *Shigella dysenteriae* serotype 1 biosynthesis polypeptides encoded by any one of SEQ ID Nos: 1 and 2, wherein the variants comprise O antigen biosynthesis polypeptide analogs, wherein one or more of the specified amino acids is deleted or replaced, or wherein one or more non-specified amino acids are added without loss of biosynthesis of *Shigella dysenteriae* serotype 1 O antigen or protective immunological activity of the O antigen biosynthesis gene product, said DNA being under the control of cognate promoters.

* * * * *

SEQUENCE LISTING

```
<160> NUMBER OF SEQ ID NOS: 17

<210> SEQ ID NO 1
<211> LENGTH: 9297
<212> TYPE: DNA
<213> ORGANISM: Shigella dysenteriae 1

<400> SEQUENCE: 1

ctctctgaat actcggtcat ccagaccaaa gaaccactgg accgtgaagg taaagtcagc     60

cgcattgttg aattcatcga aaaaccggat cagccgcaga cgctggactc agacatcatg    120

gccgttggtc gctatgtgct ttctgccgat atttggccgg aactagaacg cactcagcta    180

ggtgcatggg gacgtattca gctgactgat gccattgccg aactggcgaa aaaacagtcc    240

gttgatgcca tgctgatgac tggagacagc tacgactgcg gaaaaaaaat gggctatatg    300

caggcgtttg tgaagtatgg gctgcgcaac ctcaaagaag gggcgaagtt ccgtaaaggg    360

attgagaagc tgttaagcga ataatgaaaa tctgaccgaa tgtaacggtt gataagaaaa    420

ttataacggc agtgaagatt cgtggcgaaa gtaatttgtt gcgaatattc ctgccgttgt    480

tttatataaa caatcagaat aacaaagagt tagcaatagg attttcgtca aagttttcca    540

ggattttcct tgtttccaga gcggattggt aagacaatta gtgtttgaat ttttcgggtt    600

tagcgcgagt gggtaacgct cgtcacatcg tggacatgta tgcagtgctc tggtagctgt    660

aaagccaggg gcggtagcgt gcattaatac ctctattaat caaactgaga gccgcttatt    720

tcacagcatg ctctgaagta atatggaata ataaagtgaa gatacttgtt actggtggcg    780

caggatttat tggttctgct gtagttcgtc acattataaa taatacgcag gatagtgttg    840

ttaatgtcga taaattaacg tacgccggaa acctggagtc acttgctgat gtttctgact    900

ctaaacgcta tgtttttgaa catgcggata tttgcgatgc tgctgcaatg gcgcggattt    960

ttgctcagca tcagccggat gcagtgatgc acctggctgc tgaaagccat gtggatcgtt   1020

caattacagg ccctgcggca tttattgaaa ccaatattgt tggtacttat gtccttttgg   1080

aagcggctcg caattactgg tctgctcttg atggcgacaa gaaaaatagc ttccgttttc   1140
```

-continued

```
atcatatttc tactgacgaa gtctatggtg atttgcctca tcctgacgaa gtaaataata   1200
aagaacaatt acccctcttt actgagacga cagcttacgc gcctagtagt ccttattccg   1260
catcaaaagc atccagcgat catttagtcc gtgcgtggaa acgtacctat ggtttaccga   1320
ccattgtgac taactgttcg aataactacg gtccttatca ctttccggaa aaattgattc   1380
cactagtaat tcttaatgct ctggaaggta aggcattacc tatttatggc aaaggggatc   1440
aaattcgtga ctggctgtat gttgaagatc atgcgcgtgc gttatatatc gtcgtaaccg   1500
aaggtaaagc gggtgaaact tataacattg gtggacacaa cgaaaagaaa aacatcgatg   1560
tagtgctcac tatttgtgat ttgttggatg agattgtacc gaaagagaaa tcttaccgcg   1620
agcaaattac ttatgttgcc gatcgcccgg gacacgatcg ccgttatgcg attgatgcag   1680
agaagattag ccgcgaattg ggctggaaac cgcaggaaac gtttgagagc gggattcgta   1740
aaacggtggg atggtacctc tccaatacaa aatgggttga taatgtaaaa agtggtgcct   1800
atcaatcgtg gattgaacag aactatgagg gccgccagta atgaatatcc tccttttcgg   1860
caaaacaggg caggtaggtt gggaactaca gcgtgctctg gcacctctgg gtaatttgat   1920
tgctcttgat gttcactcca ctgattactg tggtgatttt agtaatcctg aaggtgtagc   1980
tgaaaccgta agaagcattc ggcctgatat tattgtcaac gcagccgctc acaccgcagt   2040
agacaaagca gaatcagaac cggagtttgc acaattactt aacgcgacga gtgtcgaagc   2100
gatcgcgaaa gcagccaatg aagtcggcgc ctgggttatt cactactcta ctgactacgt   2160
atttccgggg accggtgaaa taccatggca ggaggcggat gcaaccgcac cgctaaatgt   2220
ttacggtgaa accaagttag ctggagaaaa agcattacaa gagcattgtg cgaagcacct   2280
aattttccgt acaagctggg tctatgcagg taaaggaaat aacttcgcca aaacgatgtt   2340
gcgtctggga aaagagcgtg aagaattagc cgttattaat gatcagtttg gtgcgccaac   2400
aggtgctgaa ctgctggctg attgtacggc acatgcaatt cgtgtggcag tgaataaacc   2460
agaagtcgca ggcttgtacc atctggtagc cactggtacc acaacctggc acgattatgc   2520
tgcgctggtt tttgaagagg cacgaaaagc aggtattccc cttgcactca acaagctcaa   2580
cgcagtacca acaacagctt atcctacacc agctcgtcgt ccacataact ctcgccttaa   2640
tacagaaaaa tttcagcaaa attttgcgct tgttttgcct gactggcagg ttggcgtgaa   2700
acgaatgctc aacgaattat ttacgactac agcaatttaa tagtttttgc atcttgttcg   2760
tgatgatgga gcaagatgaa ttaaaaggaa tgatgtaatg aaaacgcgta aaggtattat   2820
tttagcgggt ggctctggta ctcgtcttta tcctgtgact atggctgtca gtaaacagct   2880
attacctatt tatgataagc cgatgatcta ttacccgctc tctacactga tgttggcggg   2940
tattcgcgat attctgatta ttagtacgcc acaggatact cctcgttttc aacaactcct   3000
gggtgatggt agccagtggg ggttaaatct tcagtacaaa gtgcaaccga gtccagatgg   3060
tcttgcgcag gcatttatca tcggtgaaga gtttatcggt ggtgatgatt gtgctctggt   3120
tctcggtgat aatatcttct acggtcatga tctgccgaag ttaatggatg tcgctgtcaa   3180
caaagaaagt ggtgcaacgg tatttgccta tcacgttaat gatcctgaac gctacggtgt   3240
tgttgagttt gataaaaacg gtacggcaat cagcctggaa gaaaaaccgc tacaaccaaa   3300
aagtaattat gcggtaaccg ggctttattt ctatgataac gacgttgtcg aaatggcgaa   3360
aaaccttaag ccttctgccc gtggtgaact ggaaattacc gatattaacc gtatttatat   3420
ggagcagggg cgtttatccg ttgccatgat gggacgtggt tatgcatggc tggacacggg   3480
```

-continued

```
gacacatcaa agtcttattg aagcaagcaa cttcattgca acaattgaag agcgccaagg   3540
gttaaaggta tcttgcctgg aagagattgc ttatcgtaaa ggctttattg acgcagagca   3600
ggttaatgta ttagccgaac cgctaaagaa aaatgcttat ggtcagtatc tgttgaaaat   3660
gattaaaggt tattaaaaat gaatgtaatt aaaactgaaa ttccagatgt attaattttc   3720
gagccgaaag tttttggtga tgaacgtggt ttttttatgg aaagctttaa ccagaaagtt   3780
ttcgaagagg ctgtagggcg gaaggttgaa tttgttcagg ataaccattc taaatcaact   3840
aagggtgtgt tacgcggact gcactatcag ttggaacctt atgctcaagg taaattagtt   3900
cgttgtgttg tcggtgaagt ttttgatgta gcagttgata ttcgtaaatc gtcacctaca   3960
tttgggaaat ggattggggt gaatttgtct gctgagaata agcgtcagtt gtggatacct   4020
gaaggatttg cgcatggatt tttggtgctg agtgaaacgg ctgagtttgt ttataaaaca   4080
acaaactatt acaatccaag ttttgaaaaa agtatttcat actcagatcc taccattaaa   4140
attcagtggc ccaatttaca ggatatgcat tttaaattat caaataagga tttgaatgct   4200
aagaactttt ttaatgacaa tagtttaatg caatgaagaa aaatatattg ctcttgttct   4260
tagtacatgg ggcaaattat ttgttcccgt ttatagttct tccatatcaa actcgaatat   4320
taagcatcga gacattcgca gatgtagcaa aaattcaagc cgctgtgatg cttttatctt   4380
taatcgtaaa ttatggatat aacttatcaa gtacaagagc tatagctagg gccgtatctc   4440
aagcagaaat aaataagatc tatagtgaga ctcttattgt aaaattatta ttggcaacca   4500
tttgtcttgc acttggttgc gtacatttga tgtatgtcaa agagtactca ttgatatatc   4560
cttttataat cagttcgata tatctttatg gtagtgcatt atttgctact tggttattcc   4620
aaggacttga gaaaatgaaa gcggtcgtta tagcaacaac aatcgctaaa ctgactggtg   4680
tgatacttac ttttatttta gttaagtctc caaatgatat agttgcagct ctttttacac   4740
aaaacattgg gatgtttata agtggtataa tatctattta tttggtaagg aaaaacaaat   4800
atgcaaccgt aatatgtttt cgacttaaaa atattattgt aagcttaaaa gaagcgtggc   4860
cgtttttttt atcattagct gcaacaagtg tatatacata ttttaatgtg attttattat   4920
ctttttatgc tggcgactat gttgtggcaa attttaatgc tgctgataaa ttaagaatgg   4980
ctgctcaagg gttacttatt ccaataggac aggctgtttt cccacgatta tctaaactag   5040
agggctatga atatagttct aaacttaaaa tttatgcaat aaggtatgct atttttggtg   5100
tttgcattag tgcgggactt gtatttttag gtcccatgtt aactactatt tatttaggca   5160
aagaatattc gttgtcagga gaatatcttc aaagtatgtt tttactacct gccactattt   5220
caatatcgac tatactgagt caatggatgt tgatacctca aggcaaagaa aaaatattaa   5280
gcagaatcta tattctaggc gccattgtcc atttattata tgcatttcct ttagtttact   5340
attatggggc ttggggcatg gtaatatcaa ttttatttac tgaagtctta attgtattat   5400
ttatgcttaa ggctgtgaaa tgacttactt tactggtttt attttaatat tgtttgctat   5460
tataattaaa agattaactc caagtcaaag caagaaaaat attgtcttaa tagctaatgc   5520
gttttgggga atattgttgg taggttatgc tttcaatgaa caatatttcg taccattaag   5580
tgcaacaacc ttgtttttta tacttgcatt cttatttttc tttagtatga cttatatttt   5640
aattgctagg agtggaaggg ttgtttttc tttcggtact ggttttatag aaagcaaata   5700
tatttactgg tttgctggga tgattaatat tattagtatc tgctttggca ttatcctttt   5760
atataataat catttttctt taaaagtaat gagagaagga attttagatg gttctattag   5820
tgggtttgga ttggggataa gtttgccact ttccttctgc tgtatgtatt tagcaagaca   5880
```

-continued

```
tgagaataaa aaaaattatt tctattgttt tacactactt tcattcttgc ttgcggtgtt   5940
atcaacttca aagatcttct taatattatt ccttgtatat attgttggaa taaatagtta   6000
tgtaagcaaa aagaaattgc ttatttatgg agtgtttgta tttggactgt tcgctttatc   6060
aagtattatc ttgggtaagt tctcttcaga ccctgaaggc aagattattt cagcaatatt   6120
tgatacgtta agggtttatc ttttctcggg attggcagcc tttaatcttt atgttgaaaa   6180
gaatgccacg ctccccgaaa atttactttt gtatccattt aaggaggttt gggggacgac   6240
aaaagatatt cccaaaactg atattttgcc ttggatcaac attggtgtat gggacacgaa   6300
tgtatataca gcttttgcac catggtatca gtcattggga ttatatgcag ctataattat   6360
tggtattctc ttagggtttt attacgggat atggtttagc tttcgtcaaa atttagctgt   6420
gggtttttat caaacatttt tgtgttttcc tcttttaatg ttgtttttcc aggagcatta   6480
tttgttgtca tggaaaatgc attttattta tttttatgt gcaattttat tagcgatgag    6540
aaaagcatta gagtatgaat aaatattgta tcttagtact atttaatcca gatataagtg   6600
tttttattga taatgtcaaa aagattttat ctttggatgt aagtttattt gtatatgaca   6660
attcagcaaa taaacatgca ttccttgctc tatcctcaca agagcaaaca aagataaatt   6720
acttttcgat atgtgaaaat atcggattgt cgaaagctta taatgagaca ctaaggcata   6780
ttcttgaatt taataagaat gtgaaaaata aaagcattaa tgatagtgtg ctttttctcg   6840
accaagactc tgaagttgat ttaaattcca tcaatatttt gtttgaaact atatcagcag   6900
cagagtctaa tgtgatgata gtcgcgggga atcccataag gagagatgga ctaccgtata   6960
tagattaccc ccacactgta aacaatgtaa aatttgtaat tagtagttat gctgtgtatc   7020
gcttagacgc atttagaaac atcggcttgt ttcaagaaga tttttttata gatcatatcg   7080
atagtgattt ttgttcaagg ctgataaaaa gcaattacca aattctcctt agaaaagatg   7140
cctttttta tcaaccaata ggaataaaac cattcaatct ctgtggtaga tatttattcc    7200
ctatcccatc acaacaccga acatattttc aaattagaaa tgctttttta agttacaggc   7260
gcaatggtgt tacatttaat tttttattta gggaaattgt aaatagattg attatgagta   7320
tattctcagg ccttaacgag aaagacttat tgaaacgatt gcatttatat ttaaaaggaa   7380
taaaagatgg tcttaaaatg taattcttgg ctagaagtgg gggcgttgtg attaaaaaaa   7440
aagtggcggc gataattata acatataatc cagatctaac aattctgcga gaaagttata   7500
cgagtctata taagcaagtc gataaaataa ttcttattga taacaactct acaaactatc   7560
aagaacttaa gaagttattc gaaaaaaaag aaaaaataaa aatagtgccc ttgagtgata   7620
atataggact agcagcagct caaaatttag gtttgaactt agctattaaa aataactata   7680
cttatgctat tttattcgat caggatagcg tcttacaaga caatggaatt aacagtttct   7740
tttttgaatt tgagaaatta gttagtgaag aaaaattaaa tatagttgcc attgggccaa   7800
gtttttttga cgaaaagaca ggaagacgct ttcggcctac aaaatttatc ggtccctttt   7860
tatatccctt tcgtaaaata accacaaaaa atcctctaac agaagttgac ttcttgattg   7920
cttctggttg tttcataaaa ttggagtgta ttaaatcagc cggaatgatg actgaatcgt   7980
tattcatcga ttatattgat gttgaatggt catatcgtat gcgttcgtat ggctataagc   8040
tatatattca taatgatatt cacatgagtc atttagtggg agaatctcga gttaatttag   8100
gattgaaaac tatttcttta catgggccgc taagacgata ttacttattt aggaattata   8160
tttcaatttt aaaagtgaga tatataccgt taggatataa aatacgtgag ggttttttta   8220
```

-continued atatcggaag atttttggta agtatgatta taactaaaaa tagaaaaact ttaattttat 8280
acactataaa agcaattaag gacggaataa ataatgaaat ggggaaatat aaaggctaac 8340
aacatattat gaaaaaaata atacataacc aagtgttgcc gaaaatgtct gggattcagc 8400
aaatctcttt tgatattttg tcaggtctta aagacaagga tgtacaaaaa tttatattat 8460
gcggtttacc agatggcagt tcagataatg aatttaaaaa gaaatttact gatataggtg 8520
ttagggttat tacgatacct acattaaaac gaaatatcgg gtggcatgac tttcgatgtt 8580
tcattgattt atacaatttt tttaaaaaag aaaaatttga tatagttcat acaaactcaa 8640
ctaagccagg aataatagct agaatagccg ctagattagc cgggacaaaa ctcattattc 8700
acacagtaca tggaatcgca tttcatagaa aagaaaatac tgtaaggaaa attttgcgac 8760
tctttttggt agcattaatg tgacagtgaa cgagaattat ttaaaatatt atccattcgt 8820
taaaagtcat attatatata atggagttga tttcaacgtt ctttgctgca ataaaaagga 8880
ttatgatttt ttacatattg catttatggc tagacttgat aaacaaaaaa accattggag 8940
tttataagag ccgttaatat tattaagaaa aaattaccaa atgagcgttt gaaatttaca 9000
ttagctggct gtggtgagtt agaaaatgaa tgtaaaaaat taatagaata ttttcatctt 9060
acagatgtta ttgatatgcc tggatggata gtagataaaa acacgtttta taactctgtc 9120
gatattattt gccagccatc caattgggtg gcttttggct tagtatttgt tgaggccgcc 9180
ttttttgaaa ttccatctgt ttcaaggaat atcgaaggga ttcctgaggt tattttagat 9240
aatgaaactg ggcttttgta tgagggcgga gaagccgagt tgagtgaaaa gctgata 9297

<210> SEQ ID NO 2
<211> LENGTH: 1507
<212> TYPE: DNA
<213> ORGANISM: Shigella dysenteriae 1

<400> SEQUENCE: 2
tcagcgtttt tcagaggact acatgtcatg gcttgttatc gtttataata aaaaaacaaa 60
tgtggattaa tatatggaag ggatttggtt tttctcgata aatttaactt tggagtgtca 120
gggttgagtg gtaatttatg gttgatggag aagtgggagt taaaaaatat atttaacttc 180
ttgttgaaag gtaaaataat ggcagtgcct gcgatcttgt tttctttgat aaaatatgaa 240
agaagatgcg ctttaacaaa gaaaaataaa ggtaagggta ataaataatg aagatctcaa 300
taatagggaa cacagcaaat gctatgattt tgtttagatt ggatttaata aaaacactaa 360
ccaagaaagg gatttcagtc tatgcttttg ctactgacta taatgattca tccaaggaaa 420
taataaaaaa agcaggcgcc attcctgttg attataattt aagtcgcagt ggtattaacc 480
ttgctggtga tttatggaat acttacttat taagtaaaaa actaaagaag ataaaaccag 540
atgctatttt atcttttttt tcaaagccct ctatctttgg atcgttggct ggtatttttt 600
caggcgttaa aaataataca gctatgcttg aggggttagg ttttttattt acagagcagc 660
cacatggaac tccgttaaaa acaaagttac ttaaaaatat ccaggttctc ctgtataaaa 720
taatatttcc acatatcaac tcattaatac tccttaacaa ggatgattat catgatttga 780
tagataaata caaaataaaa ttaaaatctt gccatattct tggtggcatt ggtttagata 840
tgaataatta ctgtaaaagc acgccaccaa caaatgaaat atcattcatt tttatagctc 900
gtttgctagc agaaaaagga gtcaatgagt ttgttgctgc cgcaaaaaaa ataaaaaaaa 960
cacatcccaa tgttgaattt attatacttg gcgctataga taaggaaaac cccggagggt 1020
tatctgaatc tgacgtagat actttaatta aatcaggagt tatttcttat cccggatttg 1080

-continued tttctaatgt ggctgattgg attgaaaaat caagcgtatt tgttcttcct tcctattatc 1140
gagagggagt tcctcgtagt acacaagaag cgatggctat ggggaggccg attttaacta 1200
ctaatttacc aggctgcaaa gaaacaatta ttgatggtgt gaatggatat gttgtaaaaa 1260
aatggtcaca tgaagatctt gcagaaaaaa tgctgaagtt aattaataat cctgaaaaaa 1320
taatcagtat gggagaagaa agttataagt tagcaagaga aagattcgat gcaaatgtaa 1380
ataatgtaaa gttattaaaa atactaggga ttcctgatta ataaacgaaa agcggctctg 1440
attcattcgg aactaagaac ctatctcaat aggagctaaa ttcatgacct tacccagcca 1500
tatcgat 1507

<210> SEQ ID NO 3
<211> LENGTH: 361
<212> TYPE: PRT
<213> ORGANISM: Shigella dysenteriae 1

<400> SEQUENCE: 3

Met Lys Ile Leu Val Thr Gly Gly Ala Gly Phe Ile Gly Ser Ala Val
1 5 10 15

Val Arg His Ile Ile Asn Asn Thr Gln Asp Ser Val Val Asn Val Asp
20 25 30

Lys Leu Thr Tyr Ala Gly Asn Leu Glu Ser Leu Ala Asp Val Ser Asp
35 40 45

Ser Lys Arg Tyr Val Phe Glu His Ala Asp Ile Cys Asp Ala Ala Ala
50 55 60

Met Ala Arg Ile Phe Ala Gln His Gln Pro Asp Ala Val Met His Leu
65 70 75 80

Ala Ala Glu Ser His Val Asp Arg Ser Ile Thr Gly Pro Ala Ala Phe
85 90 95

Ile Glu Thr Asn Ile Val Gly Thr Tyr Val Leu Leu Glu Ala Ala Arg
100 105 110

Asn Tyr Trp Ser Ala Leu Asp Gly Asp Lys Lys Asn Ser Phe Arg Phe
115 120 125

His His Ile Ser Thr Asp Glu Val Tyr Gly Asp Leu Pro His Pro Asp
130 135 140

Glu Val Asn Asn Lys Glu Gln Leu Pro Leu Phe Thr Glu Thr Thr Ala
145 150 155 160

Tyr Ala Pro Ser Ser Pro Tyr Ser Ala Ser Lys Ala Ser Ser Asp His
165 170 175

Leu Val Arg Ala Trp Lys Arg Thr Tyr Gly Leu Pro Thr Ile Val Thr
180 185 190

Asn Cys Ser Asn Asn Tyr Gly Pro Tyr His Phe Pro Glu Lys Leu Ile
195 200 205

Pro Leu Val Ile Leu Asn Ala Leu Glu Gly Lys Ala Leu Pro Ile Tyr
210 215 220

Gly Lys Gly Asp Gln Ile Arg Asp Trp Leu Tyr Val Glu Asp His Ala
225 230 235 240

Arg Ala Leu Tyr Ile Val Val Thr Glu Gly Lys Ala Gly Glu Thr Tyr
245 250 255

Asn Ile Gly Gly His Asn Glu Lys Lys Asn Ile Asp Val Val Leu Thr
260 265 270

Ile Cys Asp Leu Leu Asp Glu Ile Val Pro Lys Glu Lys Ser Tyr Arg
275 280 285

-continued

Glu Gln Ile Thr Tyr Val Ala Asp Arg Pro Gly His Asp Arg Arg Tyr
290 295 300

Ala Ile Asp Ala Glu Lys Ile Ser Arg Glu Leu Gly Trp Lys Pro Gln
305 310 315 320

Glu Thr Phe Glu Ser Gly Ile Arg Lys Thr Val Gly Trp Tyr Leu Ser
325 330 335

Asn Thr Lys Trp Val Asp Asn Val Lys Ser Gly Ala Tyr Gln Ser Trp
340 345 350

Ile Glu Gln Asn Tyr Glu Gly Arg Gln
355 360

<210> SEQ ID NO 4
<211> LENGTH: 299
<212> TYPE: PRT
<213> ORGANISM: Shigella dysenteriae 1

<400> SEQUENCE: 4

Met Asn Ile Leu Leu Phe Gly Lys Thr Gly Gln Val Gly Trp Glu Leu
1 5 10 15

Gln Arg Ala Leu Ala Pro Leu Gly Asn Leu Ile Ala Leu Asp Val His
20 25 30

Ser Thr Asp Tyr Cys Gly Asp Phe Ser Asn Pro Glu Gly Val Ala Glu
35 40 45

Thr Val Arg Ser Ile Arg Pro Asp Ile Ile Val Asn Ala Ala Ala His
50 55 60

Thr Ala Val Asp Lys Ala Glu Ser Glu Pro Glu Phe Ala Gln Leu Leu
65 70 75 80

Asn Ala Thr Ser Val Glu Ala Ile Ala Lys Ala Ala Asn Glu Val Gly
85 90 95

Ala Trp Val Ile His Tyr Ser Thr Asp Tyr Val Phe Pro Gly Thr Gly
100 105 110

Glu Ile Pro Trp Gln Glu Ala Asp Ala Thr Ala Pro Leu Asn Val Tyr
115 120 125

Gly Glu Thr Lys Leu Ala Gly Glu Lys Ala Leu Gln Glu His Cys Ala
130 135 140

Lys His Leu Ile Phe Arg Thr Ser Trp Val Tyr Ala Gly Lys Gly Asn
145 150 155 160

Asn Phe Ala Lys Thr Met Leu Arg Leu Gly Lys Glu Arg Glu Glu Leu
165 170 175

Ala Val Ile Asn Asp Gln Phe Gly Ala Pro Thr Gly Ala Glu Leu Leu
180 185 190

Ala Asp Cys Thr Ala His Ala Ile Arg Val Ala Val Asn Lys Pro Glu
195 200 205

Val Ala Gly Leu Tyr His Leu Val Ala Thr Gly Thr Thr Thr Trp His
210 215 220

Asp Tyr Ala Ala Leu Val Phe Glu Glu Ala Arg Lys Ala Gly Ile Pro
225 230 235 240

Leu Ala Leu Asn Lys Leu Asn Ala Val Pro Thr Thr Ala Tyr Pro Thr
245 250 255

Pro Ala Arg Arg Pro His Asn Ser Arg Leu Asn Thr Glu Lys Phe Gln
260 265 270

Gln Asn Phe Ala Leu Val Leu Pro Asp Trp Gln Val Gly Val Lys Arg
275 280 285

Met Leu Asn Glu Leu Phe Thr Thr Thr Ala Ile
290 295

<210> SEQ ID NO 5
<211> LENGTH: 292
<212> TYPE: PRT
<213> ORGANISM: Shigella dysenteriae 1

<400> SEQUENCE: 5

```
Met Lys Thr Arg Lys Gly Ile Ile Leu Ala Gly Gly Ser Gly Thr Arg
1               5                   10                  15

Leu Tyr Pro Val Thr Met Ala Val Ser Lys Gln Leu Leu Pro Ile Tyr
            20                  25                  30

Asp Lys Pro Met Ile Tyr Tyr Pro Leu Ser Thr Leu Met Leu Ala Gly
        35                  40                  45

Ile Arg Asp Ile Leu Ile Ile Ser Thr Pro Gln Asp Thr Pro Arg Phe
    50                  55                  60

Gln Gln Leu Leu Gly Asp Gly Ser Gln Trp Gly Leu Asn Leu Gln Tyr
65                  70                  75                  80

Lys Val Gln Pro Ser Pro Asp Gly Leu Ala Gln Ala Phe Ile Ile Gly
                85                  90                  95

Glu Glu Phe Ile Gly Gly Asp Asp Cys Ala Leu Val Leu Gly Asp Asn
            100                 105                 110

Ile Phe Tyr Gly His Asp Leu Pro Lys Leu Met Asp Val Ala Val Asn
        115                 120                 125

Lys Glu Ser Gly Ala Thr Val Phe Ala Tyr His Val Asn Asp Pro Glu
    130                 135                 140

Arg Tyr Gly Val Val Glu Phe Asp Lys Asn Gly Thr Ala Ile Ser Leu
145                 150                 155                 160

Glu Glu Lys Pro Leu Gln Pro Lys Ser Asn Tyr Ala Val Thr Gly Leu
                165                 170                 175

Tyr Phe Tyr Asp Asn Asp Val Val Glu Met Ala Lys Asn Leu Lys Pro
            180                 185                 190

Ser Ala Arg Gly Glu Leu Glu Ile Thr Asp Ile Asn Arg Ile Tyr Met
        195                 200                 205

Glu Gln Gly Arg Leu Ser Val Ala Met Met Gly Arg Gly Tyr Ala Trp
    210                 215                 220

Leu Asp Thr Gly Thr His Gln Ser Leu Ile Glu Ala Ser Asn Phe Ile
225                 230                 235                 240

Ala Thr Ile Glu Glu Arg Gln Gly Leu Lys Val Ser Cys Leu Glu Glu
                245                 250                 255

Ile Ala Tyr Arg Lys Gly Phe Ile Asp Ala Glu Gln Val Asn Val Leu
            260                 265                 270

Ala Glu Pro Leu Lys Lys Asn Ala Tyr Gly Gln Tyr Leu Leu Lys Met
        275                 280                 285

Ile Lys Gly Tyr
    290
```

<210> SEQ ID NO 6
<211> LENGTH: 185
<212> TYPE: PRT
<213> ORGANISM: Shigella dysenteriae 1

<400> SEQUENCE: 6

```
Met Asn Val Ile Lys Thr Glu Ile Pro Asp Val Leu Ile Phe Glu Pro
1               5                   10                  15

Lys Val Phe Gly Asp Glu Arg Gly Phe Phe Met Glu Ser Phe Asn Gln
            20                  25                  30
```

Lys Val Phe Glu Glu Ala Val Gly Arg Lys Val Glu Phe Val Gln Asp
35 40 45

Asn His Ser Lys Ser Thr Lys Gly Val Leu Arg Gly Leu His Tyr Gln
50 55 60

Leu Glu Pro Tyr Ala Gln Gly Lys Leu Val Arg Cys Val Val Gly Glu
65 70 75 80

Val Phe Asp Val Ala Val Asp Ile Arg Lys Ser Ser Pro Thr Phe Gly
85 90 95

Lys Trp Ile Gly Val Asn Leu Ser Ala Glu Asn Lys Arg Gln Leu Trp
100 105 110

Ile Pro Glu Gly Phe Ala His Gly Phe Leu Val Leu Ser Glu Thr Ala
115 120 125

Glu Phe Val Tyr Lys Thr Thr Asn Tyr Tyr Asn Pro Ser Phe Glu Lys
130 135 140

Ser Ile Ser Tyr Ser Asp Pro Thr Ile Lys Ile Gln Trp Pro Asn Leu
145 150 155 160

Gln Asp Met His Phe Lys Leu Ser Asn Lys Asp Leu Asn Ala Lys Asn
165 170 175

Phe Phe Asn Asp Asn Ser Leu Met Gln
180 185

<210> SEQ ID NO 7
<211> LENGTH: 396
<212> TYPE: PRT
<213> ORGANISM: Shigella dysenteriae 1

<400> SEQUENCE: 7

Met Lys Lys Asn Ile Leu Leu Leu Phe Leu Val His Gly Ala Asn Tyr
1 5 10 15

Leu Phe Pro Phe Ile Val Leu Pro Tyr Gln Thr Arg Ile Leu Ser Ile
20 25 30

Glu Thr Phe Ala Asp Val Ala Lys Ile Gln Ala Ala Val Met Leu Leu
35 40 45

Ser Leu Ile Val Asn Tyr Gly Tyr Asn Leu Ser Ser Thr Arg Ala Ile
50 55 60

Ala Arg Ala Val Ser Gln Ala Glu Ile Asn Lys Ile Tyr Ser Glu Thr
65 70 75 80

Leu Ile Val Lys Leu Leu Leu Ala Thr Ile Cys Leu Ala Leu Gly Cys
85 90 95

Val His Leu Met Tyr Val Lys Glu Tyr Ser Leu Ile Tyr Pro Phe Ile
100 105 110

Ile Ser Ser Ile Tyr Leu Tyr Gly Ser Ala Leu Phe Ala Thr Trp Leu
115 120 125

Phe Gln Gly Leu Glu Lys Met Lys Ala Val Val Ile Ala Thr Thr Ile
130 135 140

Ala Lys Leu Thr Gly Val Ile Leu Thr Phe Ile Leu Val Lys Ser Pro
145 150 155 160

Asn Asp Ile Val Ala Ala Leu Phe Thr Gln Asn Ile Gly Met Phe Ile
165 170 175

Ser Gly Ile Ile Ser Ile Tyr Leu Val Arg Lys Asn Lys Tyr Ala Thr
180 185 190

Val Ile Cys Phe Arg Leu Lys Asn Ile Ile Val Ser Leu Lys Glu Ala
195 200 205

Trp Pro Phe Phe Leu Ser Leu Ala Ala Thr Ser Val Tyr Thr Tyr Phe

```
    210                 215                 220

Asn Val Ile Leu Leu Ser Phe Tyr Ala Gly Asp Tyr Val Val Ala Asn
225                 230                 235                 240

Phe Asn Ala Ala Asp Lys Leu Arg Met Ala Ala Gln Gly Leu Leu Ile
                245                 250                 255

Pro Ile Gly Gln Ala Val Phe Pro Arg Leu Ser Lys Leu Glu Gly Tyr
            260                 265                 270

Glu Tyr Ser Ser Lys Leu Lys Ile Tyr Ala Ile Arg Tyr Ala Ile Phe
        275                 280                 285

Gly Val Cys Ile Ser Ala Gly Leu Val Phe Leu Gly Pro Met Leu Thr
    290                 295                 300

Thr Ile Tyr Leu Gly Lys Glu Tyr Ser Leu Ser Gly Glu Tyr Leu Gln
305                 310                 315                 320

Ser Met Phe Leu Leu Pro Ala Thr Ile Ser Ile Ser Thr Ile Leu Ser
                325                 330                 335

Gln Trp Met Leu Ile Pro Gln Gly Lys Glu Lys Ile Leu Ser Arg Ile
            340                 345                 350

Tyr Ile Leu Gly Ala Ile Val His Leu Leu Tyr Ala Phe Pro Leu Val
        355                 360                 365

Tyr Tyr Tyr Gly Ala Trp Gly Met Val Ile Ser Ile Leu Phe Thr Glu
    370                 375                 380

Val Leu Ile Val Leu Phe Met Leu Lys Ala Val Lys
385                 390                 395


<210> SEQ ID NO 8
<211> LENGTH: 380
<212> TYPE: PRT
<213> ORGANISM: Shigella dysenteriae 1

<400> SEQUENCE: 8

Met Thr Tyr Phe Thr Gly Phe Ile Leu Ile Leu Phe Ala Ile Ile Ile
1               5                   10                  15

Lys Arg Leu Thr Pro Ser Gln Ser Lys Lys Asn Ile Val Leu Ile Ala
            20                  25                  30

Asn Ala Phe Trp Gly Ile Leu Leu Val Gly Tyr Ala Phe Asn Glu Gln
        35                  40                  45

Tyr Phe Val Pro Leu Ser Ala Thr Thr Leu Phe Phe Ile Leu Ala Phe
    50                  55                  60

Leu Phe Phe Phe Ser Met Thr Tyr Ile Leu Ile Ala Arg Ser Gly Arg
65                  70                  75                  80

Val Val Phe Ser Phe Gly Thr Gly Phe Ile Glu Ser Lys Tyr Ile Tyr
                85                  90                  95

Trp Phe Ala Gly Met Ile Asn Ile Ile Ser Ile Cys Phe Gly Ile Ile
            100                 105                 110

Leu Leu Tyr Asn Asn His Phe Ser Leu Lys Val Met Arg Glu Gly Ile
        115                 120                 125

Leu Asp Gly Ser Ile Ser Gly Phe Gly Leu Gly Ile Ser Leu Pro Leu
    130                 135                 140

Ser Phe Cys Cys Met Tyr Leu Ala Arg His Glu Asn Lys Lys Asn Tyr
145                 150                 155                 160

Phe Tyr Cys Phe Thr Leu Leu Ser Phe Leu Leu Ala Val Leu Ser Thr
                165                 170                 175

Ser Lys Ile Phe Leu Ile Leu Phe Leu Val Tyr Ile Val Gly Ile Asn
            180                 185                 190
```

-continued

```
Ser Tyr Val Ser Lys Lys Lys Leu Leu Ile Tyr Gly Val Phe Val Phe
        195                 200                 205

Gly Leu Phe Ala Leu Ser Ser Ile Ile Leu Gly Lys Phe Ser Ser Asp
    210                 215                 220

Pro Glu Gly Lys Ile Ile Ser Ala Ile Phe Asp Thr Leu Arg Val Tyr
225                 230                 235                 240

Leu Phe Ser Gly Leu Ala Ala Phe Asn Leu Tyr Val Glu Lys Asn Ala
                245                 250                 255

Thr Leu Pro Glu Asn Leu Leu Leu Tyr Pro Phe Lys Glu Val Trp Gly
            260                 265                 270

Thr Thr Lys Asp Ile Pro Lys Thr Asp Ile Leu Pro Trp Ile Asn Ile
        275                 280                 285

Gly Val Trp Asp Thr Asn Val Tyr Thr Ala Phe Ala Pro Trp Tyr Gln
    290                 295                 300

Ser Leu Gly Leu Tyr Ala Ala Ile Ile Ile Gly Ile Leu Leu Gly Phe
305                 310                 315                 320

Tyr Tyr Gly Ile Trp Phe Ser Phe Arg Gln Asn Leu Ala Val Gly Phe
                325                 330                 335

Tyr Gln Thr Phe Leu Cys Phe Pro Leu Leu Met Leu Phe Phe Gln Glu
            340                 345                 350

His Tyr Leu Leu Ser Trp Lys Met His Phe Ile Tyr Phe Leu Cys Ala
        355                 360                 365

Ile Leu Leu Ala Met Arg Lys Ala Leu Glu Tyr Glu
    370                 375                 380


<210> SEQ ID NO 9
<211> LENGTH: 282
<212> TYPE: PRT
<213> ORGANISM: Shigella dysenteriae 1

<400> SEQUENCE: 9

Met Asn Lys Tyr Cys Ile Leu Val Leu Phe Asn Pro Asp Ile Ser Val
1               5                   10                  15

Phe Ile Asp Asn Val Lys Lys Ile Leu Ser Leu Asp Val Ser Leu Phe
            20                  25                  30

Val Tyr Asp Asn Ser Ala Asn Lys His Ala Phe Leu Ala Leu Ser Ser
        35                  40                  45

Gln Glu Gln Thr Lys Ile Asn Tyr Phe Ser Ile Cys Glu Asn Ile Gly
    50                  55                  60

Leu Ser Lys Ala Tyr Asn Glu Thr Leu Arg His Ile Leu Glu Phe Asn
65                  70                  75                  80

Lys Asn Val Lys Asn Lys Ser Ile Asn Asp Ser Val Leu Phe Leu Asp
                85                  90                  95

Gln Asp Ser Glu Val Asp Leu Asn Ser Ile Asn Ile Leu Phe Glu Thr
            100                 105                 110

Ile Ser Ala Ala Glu Ser Asn Val Met Ile Val Ala Gly Asn Pro Ile
        115                 120                 125

Arg Arg Asp Gly Leu Pro Tyr Ile Asp Tyr Pro His Thr Val Asn Asn
    130                 135                 140

Val Lys Phe Val Ile Ser Ser Tyr Ala Val Tyr Arg Leu Asp Ala Phe
145                 150                 155                 160

Arg Asn Ile Gly Leu Phe Gln Glu Asp Phe Phe Ile Asp His Ile Asp
                165                 170                 175

Ser Asp Phe Cys Ser Arg Leu Ile Lys Ser Asn Tyr Gln Ile Leu Leu
            180                 185                 190
```

```
Arg Lys Asp Ala Phe Phe Tyr Gln Pro Ile Gly Ile Lys Pro Phe Asn
        195                 200                 205

Leu Cys Gly Arg Tyr Leu Phe Pro Ile Pro Ser Gln His Arg Thr Tyr
    210                 215                 220

Phe Gln Ile Arg Asn Ala Phe Leu Ser Tyr Arg Arg Asn Gly Val Thr
225                 230                 235                 240

Phe Asn Phe Leu Phe Arg Glu Ile Val Asn Arg Leu Ile Met Ser Ile
                245                 250                 255

Phe Ser Gly Leu Asn Glu Lys Asp Leu Leu Lys Arg Leu His Leu Tyr
            260                 265                 270

Leu Lys Gly Ile Lys Asp Gly Leu Lys Met
        275                 280


<210> SEQ ID NO 10
<211> LENGTH: 303
<212> TYPE: PRT
<213> ORGANISM: Shigella dysenteriae 1

<400> SEQUENCE: 10

Met Ile Lys Lys Lys Val Ala Ala Ile Ile Ile Thr Tyr Asn Pro Asp
1               5                   10                  15

Leu Thr Ile Leu Arg Glu Ser Tyr Thr Ser Leu Tyr Lys Gln Val Asp
            20                  25                  30

Lys Ile Ile Leu Ile Asp Asn Asn Ser Thr Asn Tyr Gln Glu Leu Lys
        35                  40                  45

Lys Leu Phe Glu Lys Lys Glu Lys Ile Lys Ile Val Pro Leu Ser Asp
    50                  55                  60

Asn Ile Gly Leu Ala Ala Ala Gln Asn Leu Gly Leu Asn Leu Ala Ile
65                  70                  75                  80

Lys Asn Asn Tyr Thr Tyr Ala Ile Leu Phe Asp Gln Asp Ser Val Leu
                85                  90                  95

Gln Asp Asn Gly Ile Asn Ser Phe Phe Phe Glu Phe Glu Lys Leu Val
            100                 105                 110

Ser Glu Glu Lys Leu Asn Ile Val Ala Ile Gly Pro Ser Phe Phe Asp
        115                 120                 125

Glu Lys Thr Gly Arg Arg Phe Arg Pro Thr Lys Phe Ile Gly Pro Phe
    130                 135                 140

Leu Tyr Pro Phe Arg Lys Ile Thr Thr Lys Asn Pro Leu Thr Glu Val
145                 150                 155                 160

Asp Phe Leu Ile Ala Ser Gly Cys Phe Ile Lys Leu Glu Cys Ile Lys
                165                 170                 175

Ser Ala Gly Met Met Thr Glu Ser Leu Phe Ile Asp Tyr Ile Asp Val
            180                 185                 190

Glu Trp Ser Tyr Arg Met Arg Ser Tyr Gly Tyr Lys Leu Tyr Ile His
        195                 200                 205

Asn Asp Ile His Met Ser His Leu Val Gly Glu Ser Arg Val Asn Leu
    210                 215                 220

Gly Leu Lys Thr Ile Ser Leu His Gly Pro Leu Arg Arg Tyr Tyr Leu
225                 230                 235                 240

Phe Arg Asn Tyr Ile Ser Ile Leu Lys Val Arg Tyr Ile Pro Leu Gly
                245                 250                 255

Tyr Lys Ile Arg Glu Gly Phe Phe Asn Ile Gly Arg Phe Leu Val Ser
            260                 265                 270

Met Ile Ile Thr Lys Asn Arg Lys Thr Leu Ile Leu Tyr Thr Ile Lys
```

```
        275                 280                 285

Ala Ile Lys Asp Gly Ile Asn Asn Glu Met Gly Lys Tyr Lys Gly
    290                 295                 300


<210> SEQ ID NO 11
<211> LENGTH: 144
<212> TYPE: PRT
<213> ORGANISM: Shigella dysenteriae 1

<400> SEQUENCE: 11

Met Lys Lys Ile Ile His Asn Gln Val Leu Pro Lys Met Ser Gly Ile
1               5                   10                  15

Gln Gln Ile Ser Phe Asp Ile Leu Ser Gly Leu Lys Asp Lys Asp Val
            20                  25                  30

Gln Lys Phe Ile Leu Cys Gly Leu Pro Asp Gly Ser Ser Asp Asn Glu
        35                  40                  45

Phe Lys Lys Lys Phe Thr Asp Ile Gly Val Arg Val Ile Thr Ile Pro
    50                  55                  60

Thr Leu Lys Arg Asn Ile Gly Trp His Asp Phe Arg Cys Phe Ile Asp
65                  70                  75                  80

Leu Tyr Asn Phe Phe Lys Lys Glu Lys Phe Asp Ile Val His Thr Asn
                85                  90                  95

Ser Thr Lys Pro Gly Ile Ile Ala Arg Ile Ala Ala Arg Leu Ala Gly
            100                 105                 110

Thr Lys Leu Ile Ile His Thr Val His Gly Ile Ala Phe His Arg Lys
        115                 120                 125

Glu Asn Thr Val Arg Lys Ile Leu Arg Leu Phe Leu Val Ala Leu Met
    130                 135                 140


<210> SEQ ID NO 12
<211> LENGTH: 377
<212> TYPE: PRT
<213> ORGANISM: Shigella dysenteriae 1

<400> SEQUENCE: 12

Met Lys Ile Ser Ile Ile Gly Asn Thr Ala Asn Ala Met Ile Leu Phe
1               5                   10                  15

Arg Leu Asp Leu Ile Lys Thr Leu Thr Lys Lys Gly Ile Ser Val Tyr
            20                  25                  30

Ala Phe Ala Thr Asp Tyr Asn Asp Ser Ser Lys Glu Ile Ile Lys Lys
        35                  40                  45

Ala Gly Ala Ile Pro Val Asp Tyr Asn Leu Ser Arg Ser Gly Ile Asn
    50                  55                  60

Leu Ala Gly Asp Leu Trp Asn Thr Tyr Leu Leu Ser Lys Lys Leu Lys
65                  70                  75                  80

Lys Ile Lys Pro Asp Ala Ile Leu Ser Phe Phe Ser Lys Pro Ser Ile
                85                  90                  95

Phe Gly Ser Leu Ala Gly Ile Phe Ser Gly Val Lys Asn Asn Thr Ala
            100                 105                 110

Met Leu Glu Gly Leu Gly Phe Leu Phe Thr Glu Gln Pro His Gly Thr
        115                 120                 125

Pro Leu Lys Thr Lys Leu Leu Lys Asn Ile Gln Val Leu Leu Tyr Lys
    130                 135                 140

Ile Ile Phe Pro His Ile Asn Ser Leu Ile Leu Leu Asn Lys Asp Asp
145                 150                 155                 160

Tyr His Asp Leu Ile Asp Lys Tyr Lys Ile Lys Leu Lys Ser Cys His
```

-continued

```
                165                 170                 175

Ile Leu Gly Gly Ile Gly Leu Asp Met Asn Asn Tyr Cys Lys Ser Thr
            180                 185                 190

Pro Pro Thr Asn Glu Ile Ser Phe Ile Phe Ile Ala Arg Leu Leu Ala
        195                 200                 205

Glu Lys Gly Val Asn Glu Phe Val Ala Ala Ala Lys Lys Ile Lys Lys
    210                 215                 220

Thr His Pro Asn Val Glu Phe Ile Ile Leu Gly Ala Ile Asp Lys Glu
225                 230                 235                 240

Asn Pro Gly Gly Leu Ser Glu Ser Asp Val Asp Thr Leu Ile Lys Ser
                245                 250                 255

Gly Val Ile Ser Tyr Pro Gly Phe Val Ser Asn Val Ala Asp Trp Ile
            260                 265                 270

Glu Lys Ser Ser Val Phe Val Leu Pro Ser Tyr Tyr Arg Glu Gly Val
        275                 280                 285

Pro Arg Ser Thr Gln Glu Ala Met Ala Met Gly Arg Pro Ile Leu Thr
    290                 295                 300

Thr Asn Leu Pro Gly Cys Lys Glu Thr Ile Ile Asp Gly Val Asn Gly
305                 310                 315                 320

Tyr Val Val Lys Lys Trp Ser His Glu Asp Leu Ala Glu Lys Met Leu
                325                 330                 335

Lys Leu Ile Asn Asn Pro Glu Lys Ile Ile Ser Met Gly Glu Glu Ser
            340                 345                 350

Tyr Lys Leu Ala Arg Glu Arg Phe Asp Ala Asn Val Asn Asn Val Lys
        355                 360                 365

Leu Leu Lys Ile Leu Gly Ile Pro Asp
    370                 375
```

<210> SEQ ID NO 13
<211> LENGTH: 28
<212> TYPE: DNA
<213> ORGANISM: Artificial Sequence
<220> FEATURE:
<223> OTHER INFORMATION: synthetic primer

<400> SEQUENCE: 13
ttatttccag actccagctg tcattatg 28

<210> SEQ ID NO 14
<211> LENGTH: 27
<212> TYPE: DNA
<213> ORGANISM: Artificial Sequence
<220> FEATURE:
<223> OTHER INFORMATION: synthetic primer

<400> SEQUENCE: 14
ccatcgatat tggctgggta aggtcat 27

<210> SEQ ID NO 15
<211> LENGTH: 45
<212> TYPE: DNA
<213> ORGANISM: Artificial Sequence
<220> FEATURE:
<223> OTHER INFORMATION: synthetic primer

<400> SEQUENCE: 15
cgtatgtcga ctgagctctc tgaatactct gtcatccaga ccaaa 45

<210> SEQ ID NO 16

-continued

```
<211> LENGTH: 40
<212> TYPE: DNA
<213> ORGANISM: Artificial Sequence
<220> FEATURE:
<223> OTHER INFORMATION: synthetic primer

<400> SEQUENCE: 16

tatcagcttt tcactcaact cggcggatcc gccctcatac                        40


<210> SEQ ID NO 17
<211> LENGTH: 39
<212> TYPE: DNA
<213> ORGANISM: Shigella

<400> SEQUENCE: 17

cagtggctct ggtagctgta aagccagggg cggtagcgt                         39
```